US006356873B1

(12) United States Patent
Teagarden et al.

(10) Patent No.: US 6,356,873 B1
(45) Date of Patent: *Mar. 12, 2002

(54) COMPUTER IMPLEMENTED PATIENT MEDICATION REVIEW SYSTEM AND PROCESS FOR THE MANAGED CARE, HEALTH CARE AND/OR PHARMACY INDUSTRY

(75) Inventors: J. Russel Teagarden, Brookfield, CT (US); Michael Clotz, Hilliard, OH (US); David Angaran, Powell, OH (US); Charlotte Kenreigh, Westerville, OH (US)

(73) Assignee: Merck-Medco Managed Care, LLC, Montvale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/437,157

(22) Filed: Nov. 10, 1999

Related U.S. Application Data

(63) Continuation of application No. 09/053,349, filed on Apr. 2, 1998.

(51) Int. Cl.[7] .............................................. G06F 17/60
(52) U.S. Cl. .................... 705/3; 705/1; 705/2; 705/500
(58) Field of Search ................................ 705/3, 1, 500, 705/2

(56) References Cited

U.S. PATENT DOCUMENTS

| | | | |
|---|---|---|---|
| 4,839,822 A | * | 6/1989 | Dormond et al. |
| 5,301,105 A | * | 4/1994 | Cummings, Jr. et al. ....... 705/2 |
| 5,583,758 A | * | 12/1996 | McIlroy et al. ................ 705/2 |

(List continued on next page.)

FOREIGN PATENT DOCUMENTS

| | | | | |
|---|---|---|---|---|
| WO | WO 94/07210 | * | 3/1994 | ........... G06F/15/42 |
| WO | WO 97/11635 | * | 4/1997 | ............ A61B/5/00 |

OTHER PUBLICATIONS http://www.med.univ-rennes1.fr/cerf/publi/ADM_index1.html?clkd=iwm, "Computer Assisted Medical Diagnosis using the Web".*
wysiwyg://299/http://www.cdc.gov/incidod/eid/vol5no6/subramanyan.htm?clkd=iwm, "Using automated Pharmacy records to Assess the Management of Tuberculosis".*

Primary Examiner—Sam Rimell
Assistant Examiner—Akiba Robinson-Boyce
(74) Attorney, Agent, or Firm—Irah H. Donner; Hale and Dorr LLP

(57) ABSTRACT

An interactive computer assisted method reviews, and analyzes, a patient one or more medications using a computer and a user associated therewith. The method includes the steps of pre-selecting patients to obtain a preliminary set of patients eligible for the interactive computer assisted method responsive to first predetermined criteria, and filtering the preliminary set of patients to identify and form a secondary set of patients from the preliminary set of patients having a greater likelihood of benefiting from the interactive computer assisted method responsive to second predetermined criteria. The method also includes the steps of enrolling a patient from the secondary set of patients, and communicating with the patient to obtain information to assist the user in determining whether therapy and/or medication issues are relevant. The method also includes the steps of preliminarily evaluating whether the therapy and medication issues are relevant responsive to the information, and communicating to a physician same. The method also includes the steps of determining whether the therapy and/or medication issues are relevant, and suggesting therapy changes, medication changes, or no changes for the patient.

20 Claims, 20 Drawing Sheets

U.S. PATENT DOCUMENTS

| | | | |
|---|---|---|---|
| 5,594,638 A | * 1/1997 | Iliff | 705/3 |
| 5,660,176 A | * 8/1997 | Iliff | |
| 5,758,095 A | 5/1998 | Albaum et al. | 705/2 |
| 5,764,923 A | * 6/1998 | Tallman et al. | 705/3 |
| 5,799,981 A | * 9/1998 | Tung et al. | |
| 5,827,180 A | * 10/1998 | Goodman | |
| 5,933,136 A | * 8/1999 | Brown | 345/327 |
| 5,956,689 A | * 9/1999 | Everhart, III | 705/3 |
| 6,014,631 A | * 1/2000 | Teagarden et al. | 705/3 |
| 6,047,259 A | * 4/2000 | Campbell et al. | 705/3 |

* cited by examiner

COMPUTER IMPLEMENTED PATIENT MEDICATION REVIEW SYSTEM AND PROCESS FOR THE MANAGED CARE, HEALTH CARE AND/OR PHARMACY INDUSTRY

This application is a continuation of U.S. application Ser. No. 09/053,349, filed Apr. 2, 1998, which is incorporated herein by reference.

BACKGROUND OF THE INVENTION

1. Field of the Invention

The present invention generally relates to a computer implemented and/or assisted process for controlling drug or health care spending and/or use while improving or maintaining the quality of care in a patient population. More particularly, the present invention relates to a computer implemented and/or assisted process for ensuring and/or designing appropriate patient care, through the selection and/or collection of extensive information on a patient's use of medication(s), medical history, and/or satisfaction, as well as the involvement of both the patient and physician in the decision-making process. The patient may optionally be, for example, using multiple medications for treatment of multiple diseases in the computer implemented and/or assisted process.

2. Background of the Related Art

Health care costs currently represent a significant portion of the United States Gross National Product, and continue to rise at an exceptional pace. A significant portion of these increased costs represents an inability to appropriately coordinate or target the appropriate medications and/or treatment for individual patients. Accordingly, we have determined that many people are deprived of access to services which can coordinate the most needed medical care and information.

Coupled with the inability to prescribe the appropriate medication and/or treatment, many people delay in obtaining, or are prevented from seeking, medical attention because of cost, time constraints, or inconvenience. If the public had universal, unrestricted and easy access to medical information, many diseases could be prevented. Similarly, the early detection and treatment of numerous diseases could keep many patients from reaching the advanced stages of illness. These advanced stages of illness are a significant part of the costs attributed to our nation's health care system. It is obvious that the United States, and the world is facing health-related issues of enormous proportions.

One prior attempt at a solution to the health care problem is called Ask-A-Nurse, wherein a group of nurses provide health information by telephone around-the-clock. A person with a medical problem calls an 800 number and describes the problem to the nurse. The nurse uses a computer for general or diagnostic information on the ailment or complaint mentioned by the caller. The nurse may then refer the caller to a doctor from a computerized referral list for a contracting hospital or group of hospitals. Client hospitals contract with Ask-A-Nurse to provide patient referrals. A managed care option called Personal Health Advisor is similar and adds the capability for the caller to hear prerecorded messages on health topics 24 hours a day.

Several problems exist with these prior medical advice systems. First, these systems have high costs associated with having a nurse answer each telephone call. Second, the caller may have to belong to a participating health plan to utilize the service. Third, and significantly, this system is designed to respond to reactive problems determined by the caller, and therefore, provides no ability to eliminate the possibility of such a condition occurring in the first instance. Fourth, these medical advice systems generally do not possess the requisite in-depth knowledge to provide meaningful guidance in any specific area, e.g., drug use.

Another prior health system provides a computerized service that answers health care questions and advises people in their homes. A health maintenance organization (HMO) may provide this service to its members in a particular geographic area. To get advice at home, an HMO member connects a toaster-sized box to a telephone and calls a toll-free 800 number. Using a keyboard that is part of the box, the user answers questions displayed on a screen of the box relating to the user's symptoms. Depending on the answers, the user might be told to try a home remedy, be called by a nurse or doctor, or be given an appointment to be examined. This system is also designed to respond to reactive problems determined by the caller, and therefore, provides no ability to eliminate the possibility of such a condition occurring in the first instance.

At the other end of the spectrum, are various attempts at analyzing retroactively using hindsight, the appropriateness of the delivered medical care for quality and cost. For example, U.S. Pat. No. 5,544,044 to Leatherman, incorporated herein by reference, relates to a software-based medical information system performs a method of analyzing health care claims records for an enrolled population (e.g., HMO, Medicaid) to assess and report on quality of care based on conformance to nationally recognized medical practice guidelines or quality indicators. FIGS. 1a–1d are flow charts illustrating this software-based medical information system that analyzes health care claims records to assess and report on quality of care.

The process is typically performed at the request of a customer that is a health maintenance organization, indemnity insurer (e.g., Blue Cross), a large, self-insured employer group or a government program (e.g., Medicaid). At the start 1, the first step 3 is to obtain the customer specific parameters, such as what time period the customer wishes to analyze or whether the customer wants to have some data broken down by particular providers or other grouping variables. The next step 4 is to update the system options and parameters using the customer specifications. Thereafter, the system obtains and loads 5 the customer data, usually consisting of the customer's already-computerized health care claims data for a specified period, together with enrollment data and health care provider data.

The enrollment data is extracted 7 so as to identify the enrollees served by the customer that meet a predefined enrollment criterion. The resulting enrollment data 9 contains one record per enrollee. Next, the relevant claims data are extracted 11 from the complete customer data base and are configured through linkages to produce the necessary health records. The claims data will include claims records for medical professional services 12 (outpatient records), claims records for hospital services 13 (inpatient records) and claims records for pharmacy purchases 14 (pharmacy records).

If the customer desires, provider-specific data is also extracted 16 from the customer data, permitting the later analysis to be broken down by the particular provider of services or products, which may be a particular doctor, clinic or hospital. The resulting files are merged 19 to produce uncorrected master files 21. Duplicate claims are excluded 23 and claims that have been reversed through the claims adjudication process. This produces a master file 25 of health care claims records.

Step 29 involves the application of the definitions for the health care condition to identify the population having that condition, followed by an analysis of the claims records for that population (a subset of the master files 25) under the defined quality care criteria. The result of the analysis in step 29 is a report that includes: charts and graphs 31 reporting statistically observed quality of care data in the population defined as having the health care condition of interest; a written analysis reporting, from a care quality viewpoint, statistical results considered worthy of highlighting 33, 35; and a report containing recommendations for actions to improve health care quality 37, 39.

Analysis for multiple health care conditions takes place iteratively through the software at step 41, and the process just described, comprising steps 29, 31, 33, and 37 and producing charts and graphs 31 and reports 35, 39 is repeated, using the next health care condition definition to identify the population having that condition, followed by an analysis of the claims records for that population under the defined quality care criteria for that next condition. After all the specified health care conditions have been processed in this manner, the reports for each condition are assembled 43 into a claims-based quality report 45 that is presented to the customer 47.

At step 51, the system recognizes whether there is the need for detailed analysis. If no such need exists, no further data collection or analysis occurs. However, if a need for detailed analysis of any health care condition has been determined, then the population identified as having that condition is subjected to sampling 55 to determine for which enrollees additional medical records information will be collected. With the provider's consent, the medical records are abstracted 59 with a particular focus on events that relate to the particular health care condition under study, resulting in a completed medical records abstract form 61.

This abstracted information is then entered into the system 63, via personal computer to produce a medical record abstract data file 65. Charts and graphs reporting statistically observed data in the population defined as having the health care condition of interest 69 and a report containing recommendations for actions to improve health care quality 71, 73. If detailed analysis of medical records is specified for multiple health care conditions, then the preceding steps are repeated until charts and graphs reporting statistically observed data 69 and a report containing recommendations for actions to improve health care quality 71, 73 are developed for each health care condition.

After all the specified health care conditions have been processed in this manner, the reports for each condition are assembled 77 into a detail level report 79 that is presented to the customer 81, and the process ends 83. However, one major drawback of this system is that it analyzes "after-the-fact" the appropriateness of the delivered medical care for quality and cost.

U.S. Pat. No. 5,660,176 to Iliff, incorporated herein by reference, is directed to a computerized medical diagnostic and treatment advice system. Referring to FIG. 2, the components of the computerized medical diagnostic and treatment advice system 100 are shown. A personal computer (PC) 102 includes a plurality of components within an enclosure 104. A plurality of telephone lines 106 interface the public telephone network 108 to the computer 102. One of telephone lines 106 is shown to be switched via network 108 to connect with a telephone 110 that is used by a person desiring medical advice (user) 112.

The system runs on the PC 102 with a microprocessor. Telephony functions use a voice processing board 122 based on a digital signal processor (DSP). A group of one to four telephone lines 106 connect to the VP board 122. The computer 102 may include a plurality of VP boards 122 based on how many phone line connections are desired for the system 100. Speech recognition is achieved using Voice Processing Corporation's speech recognition VPRO-4 board 124 (also DSP based).

The VR board 124 and the VP board 122 both connect to an industry standard architecture (ISA) bus 126. The VP board 122 also connects to a VPRO-Adapt board 128 via an analog audio bus 130 that is called Analog Extension Bus. The Adapt board 128 further connects to a digital audio bus 132. The VR board 124 also connects to the digital audio bus 132. The Adapt board 128 performs analog to digital signal conversion to a VPC-proprietary digital pulse code modulation (PCM) format.

A video adapter board 136, preferably at VGA or better resolution, interconnects to a video monitor 138. A serial communication circuit 140 interfaces a pointing device, such as a mouse 142. A parallel communication circuit may be used in place of circuit 140 in another embodiment. A keyboard controller circuit 144 interfaces a keyboard 146. A small computer systems interface (SCSI) adapter provides a SCSI bus 150 to which a 500 Mb or greater hard disk drive 152 is attached.

The hard drive 152 stores database files such as the patient files, speech files, and binary support files. Main memory 156 connects to the microprocessor 120. An algorithm processor 160 includes a parser and supporting functions that manipulate a memory variable symbol table and a run time stack.

FIG. 3 is a block diagram illustrating a conceptual view of the database files and processes of the system of FIG. 2. Patient login process 250 is used to identify a patient who has previously registered into the system. Art assistant login process 272 is used to identify an assistant who has previously registered into the system. An assisted patient login process 276 is used to identify a patient who has previously registered into the system.

If the caller is the patient, a patient registration process 252 is used to register new or first-time patients. If the caller is not the patient, an assistant registration process 274 is used to register new or first-time assistants. Then, if the patient is not already registered, an assisted patient registration process 278 is used to register the patient.

The master patient and assistant enrollment database 260 is created at run-time by one of the registration processes 252, 274, or 278. This database 260 is read by the patient login process 250 or the assisted patient login process 276 to validate a patient's identity at login time, and by the assistant login process 272 to validate an assistant's identity at login time. The database 260 is essentially a master file of all registered patients and assistants indexed by their patient ID number or assistant ID number, respectively.

In Iliff, the medical advice is provided to the general public over a telephone network. Two new authoring languages, interactive voice response and speech recognition, are used to enable expert and general practitioner knowledge to be encoded for access by the public. Meta functions for time-density analysis of a number of factors regarding the number of medical complaints per unit of time are an integral part of the system. Thus, the system in Iliff is also designed as a reactive measure to respond to caller complaints, and provides no process for ensuring and/or designing appropriate patient care, through the selection and/or collection of extensive information on a patient's use of medication(s), medical history, and/or satisfaction.

U.S. Pat. No. 4,839,822 to Dormond et al., incorporated herein by reference, relates to a computer system and method for suggesting treatments for physical trauma. FIG. 4 is a block diagram illustrating the structure of the expert system. The expert system 201, includes an inference engine and processor 210, inference interface 211, application program 212 and application interface 213. The inference engine and processor 210 functions as in an inference engine, under the control of an inference engine program, and also executes the application program 212, when necessary to perform application program functions, under the overall control of the inference engine.

Communication between the expert system and the user is by way of a CRT/keyboard 215 and through the inference interface 211, for communicating with the inference engine and processor 210, and by way of application interface 213, for communicating with the application program 212. The inference engine and processor 210 receives information from two data bases, namely a knowledge base 216, and a data base of working files 218 which are generated by the application program 212, based on information elicited from the user. A procedures and classification data base 220, input-output graphics 222 and classification graphics 224, are provided for the purpose of gathering the requisite patient and trauma information from the system user, and assembling that information into the working files 218.

In Dormond et al., the application program is executed in the computing device and interactively displays a series of screens including at least some of the graphical illustrations, to elicit responses from the user concerning the specific types of physical trauma and specific characteristics of the patient. The inference engine program, which is also executed in the computing device, uses the knowledge base and information related to the responses elicited from the user, for selecting one or more suggested treatments. The application program presents the suggested treatments to the user after execution of the inference engine program. However, the Dormond et al. system does not generally address issues relating to optimizing, coordinating and/or providing information about medication therapy, for example, when multiple medications are used, nor address coordination of such therapy with the appropriate individuals.

Accordingly, we have determined that it is desirable to provide a method and/or system to optimize or coordinate medication and/or health care therapy, for example, when multiple medications are used and/or when multiple prescribers have been involved.

We have also determined that it is desirable to provide a method and/or system that coordinates medication and/or health care therapy for the appropriate individuals or patients.

We have also determined that it is desirable to provide a method and/or system that proactively determines a patient target population to selectively apply the above medication and/or health care therapy, for better utilization of resources in conducting same.

We have also determined that it is desirable to provide a method and/or system that dynamically or in real-time analyzes the appropriateness of the delivered medication and/or health care therapy for appropriateness, quality and/or cost.

We have also determined that it is desirable to provide a method and/or system that ensures and/or designs and/or coordinates appropriate patient care, through the selection and/or collection of extensive information on a patient's use of medication(s), medical history, and/or satisfaction.

We have also determined that it is desirable to provide a method and/or system that minimizes the possibility of the occurrence of adverse health conditions in the first instance using proactive medication therapy.

We have also determined that it is desirable to provide a computer implemented and/or assisted process for ensuring and/or designing appropriate patient care, through the selection and/or collection of extensive information on a patient's use of, for example, medications, medical history, and/or satisfaction, as well as the involvement of both the patient and physician in the decision-making process.

We have also determined that it is desirable to provide a method and/or system that lowers costs of health care therapy, by dynamically or in real-time analyzing the appropriateness of the delivered medication and/or health care therapy for appropriateness, quality and/or cost, and by reducing fragmentation of prescriptions and/or improving efficiency of drug use.

SUMMARY OF THE INVENTION

It is therefore a feature and advantage of the present invention in providing a method and/or system to optimize medication and/or health care therapy, for example, when multiple medications are used.

It is another feature and advantage of the present invention in providing a method and/or system that coordinates medication and/or health care therapy for the appropriate individuals or patients.

It is another feature and advantage of the present invention in providing a method and/or system that proactively determines a patient target population to selectively apply the above medication and/or health care therapy, for better utilization of resources in conducting same.

It is another feature and advantage of the present invention in providing a method and/or system that dynamically or in real-time analyzes the appropriateness of the delivered medication and/or health care therapy for appropriateness, quality and/or cost.

It is another feature and advantage of the present invention in providing a method and/or system that ensures and/or designs appropriate patient care, through the selection and/or collection of extensive information on a patient's use of medication(s), medical history, and/or satisfaction.

It is another feature and advantage of the present invention in providing a method and/or system that minimizes the possibility of the occurrence of adverse health conditions in the first instance using proactive medication therapy.

It is another feature and advantage of the present invention in providing a computer implemented and/or assisted process for ensuring and/or designing appropriate patient care, through the selection and/or collection of extensive information on a patient's use of medication(s), medical history, and/or satisfaction, as well as the involvement of both the patient and physician in the decision-making process.

The present invention is based, in part, in our discovery of the greatly enhanced benefits resulting from combining various individuals that participate in the administering or receiving of medication and/or health care therapy in a substantially unitary or combined process. We have observed that exceptional results in terms of patient health are possible when both the patient and physician (and optionally the pharmacist for medication therapy) are involved in the decision-making process.

We have also discovered that an important feature of the present invention is being able to carry the above processes includes a computer implemented process of patient selection for the candidates most likely to benefit from the process described herein, as well as collection of extensive information on a patient's use of medication(s), medical history, and/or satisfaction. The implementation and/or assistance of the computer for the process and system described herein greatly facilitates the efficient implementation of the present invention.

The patient medication and/or health care review of the present invention (hereinafter patient medication review or patient review) is a computer assisted and/or implemented program designed to gather the therapeutic history of patients, optionally over the telephone. The review provides, for example, a complete history of medication use, adverse effects, treatment goals, medical history, and patient concerns and satisfaction. The program integrally involves, inter alia, the patient's physician to verify current medications, discuss potential interventions and discuss any compliance issues.

The patient medication review goals are to improve or maintain patient care, while controlling or reducing drug spending, and increasing patient involvement in medication discussions. This. patient review process ensures appropriate patient care through the collection of extensive information on a patient's use of, for example, the medication(s), medical history, and satisfaction, as well as the involvement of both the patient and physician in the decision-making process.

To achieve the above and other features and advantages of the present invention, an interactive computer assisted method reviews, analyzes, and optionally prescribes a patient one or more medications using a computer and a user associated therewith. The method includes the steps of pre-selecting, by the computer, patients to obtain a preliminary set of patients eligible for the interactive computer assisted method responsive to first predetermined criteria, and filtering, by the computer, the preliminary set of patients to identify and form a secondary set of patients from the preliminary set of patients having a greater likelihood of benefiting from the interactive computer assisted method responsive to second predetermined criteria. The method also includes the steps of enrolling, by the computer, at least one patient from the secondary set of patients, and communicating, by the computer, with the at least one patient to obtain information to assist the user in determining whether at least one of therapy and medication changes and/or issues are appropriate. The method also includes the steps of preliminarily evaluating, by the computer, whether the at least one of therapy and medication changes are appropriate, relevant and/or actionable, responsive to the information, and communicating, by the computer, to a physician, the at least one of therapy and medication changes and the information. The method also includes the steps of determining, by the physician, whether the at least one of therapy and medication changes are appropriate responsive to the information, and prescribing at least one of the at least one of therapy and medication changes, at least one of other therapy and medication changes, and no therapy and medication changes for the at least one patient.

In accordance with another embodiment of the invention, an interactive computer assisted method reviews, analyzes, and optionally prescribes a patient one or more medications using a computer and a user associated therewith. The method includes the steps of pre-selecting, by the computer, patients to obtain a preliminary set of patients eligible for the interactive computer assisted method responsive to first predetermined criteria, and filtering, by at least one of the user and the computer, the preliminary set of patients to identify and form a secondary set of patients from the preliminary set of patients having a greater likelihood of benefiting from the interactive computer assisted method responsive to second predetermined criteria. The method also includes the steps of enrolling, by the at least one of the user and the computer, at least one patient from the secondary set of patients, and communicating, by the at least one of the user and the computer, with the at least one patient to obtain information to assist the user in determining whether at least one of therapy and medication changes are appropriate. The method also includes the steps of preliminarily evaluating, by the at least one of the user and the computer, whether the at least one of therapy and medication changes are appropriate responsive to the information, and communicating, by the at least one of the user and the computer, to a physician, the at least one of therapy and medication changes and the information. The method also includes the steps of determining, by the physician, whether the at least one of therapy and medication changes are appropriate responsive to the information, and prescribing at least one of the at least one of therapy and medication changes, at least one of other therapy and medication changes, and no therapy and medication changes for the at least one patient.

In accordance with another embodiment of the invention, an interactive computer assisted method reviews, analyzes, and optionally prescribes a patient one or more medications using a computer and a user associated therewith. The method includes the steps of pre-selecting patients to obtain a preliminary set of patients eligible for the interactive computer assisted method responsive to first predetermined criteria, and filtering the preliminary set of patients to identify and form a secondary set of patients from the preliminary set of patients having a greater likelihood of benefiting from the interactive computer assisted method responsive to second predetermined criteria. The method also includes the steps of enrolling at least one patient from the secondary set of patients, and communicating with the at least one patient to obtain information to assist the user in determining whether at least one of therapy and medication changes are appropriate. The method also includes the steps of preliminarily evaluating whether the at least one of therapy and medication changes are appropriate responsive to the information, and communicating to a physician, the at least one of therapy and medication changes and the information. The method also includes the steps of determining whether the at least one of therapy and medication changes are appropriate responsive to the information, and prescribing at least one of the at least one of therapy and medication changes, at least one of other therapy and medication changes, and no therapy and medication changes for the at least one patient.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

FIGS. 1a–1d are flow charts depicting the overall operation of the method of

Notations and Nomenclature

Figure 1A:
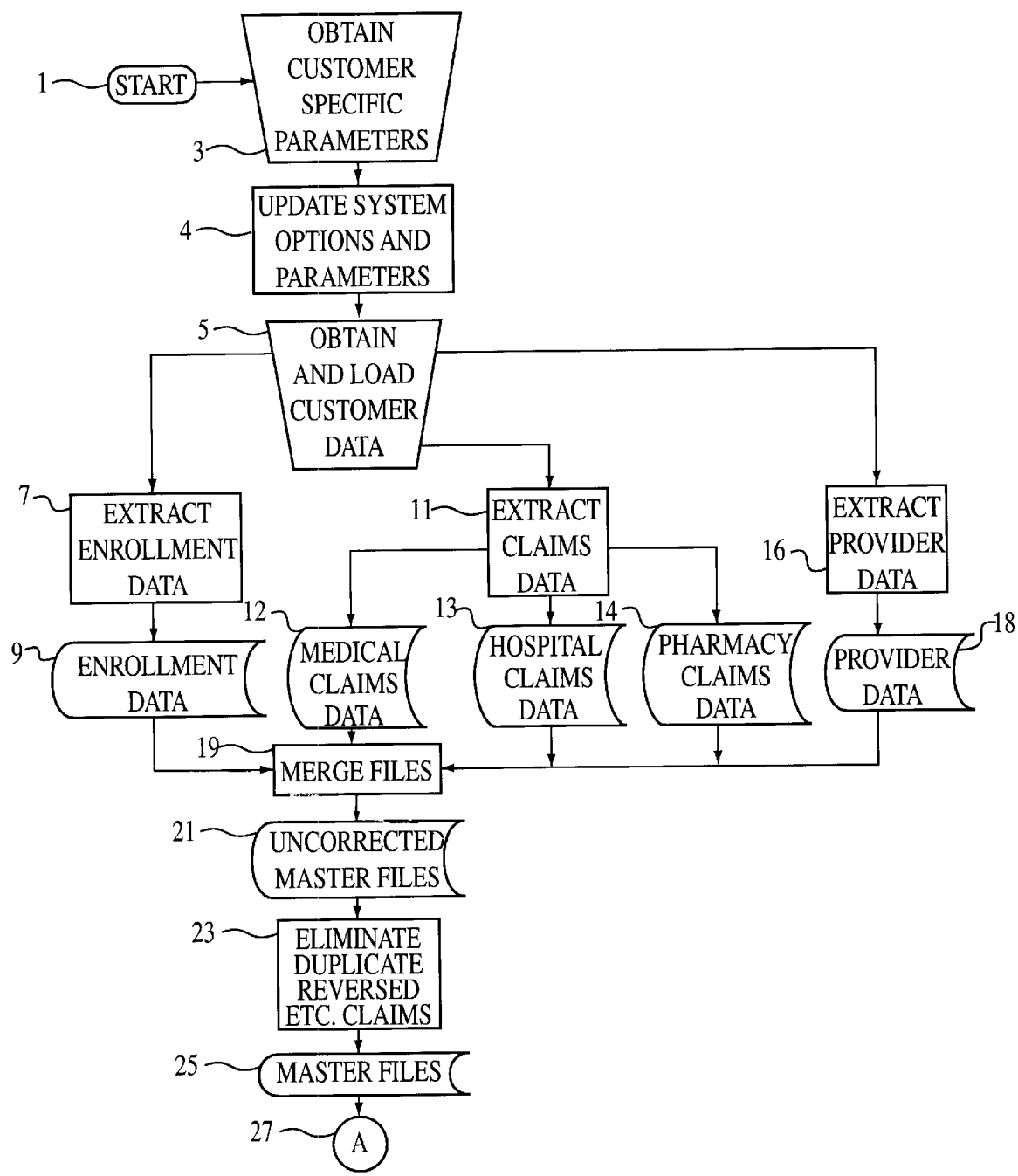
Figure 1B:
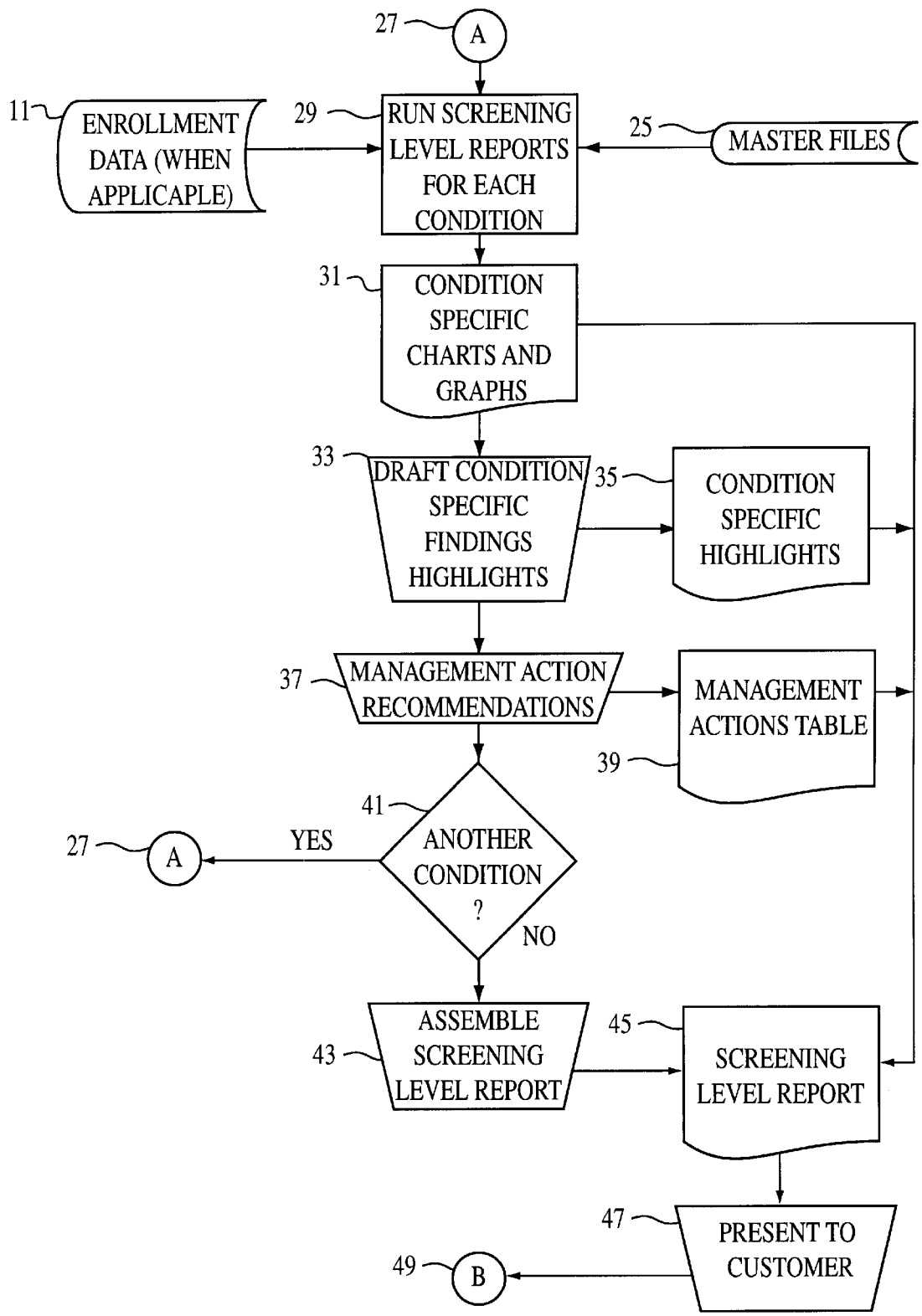
Figure 1C:
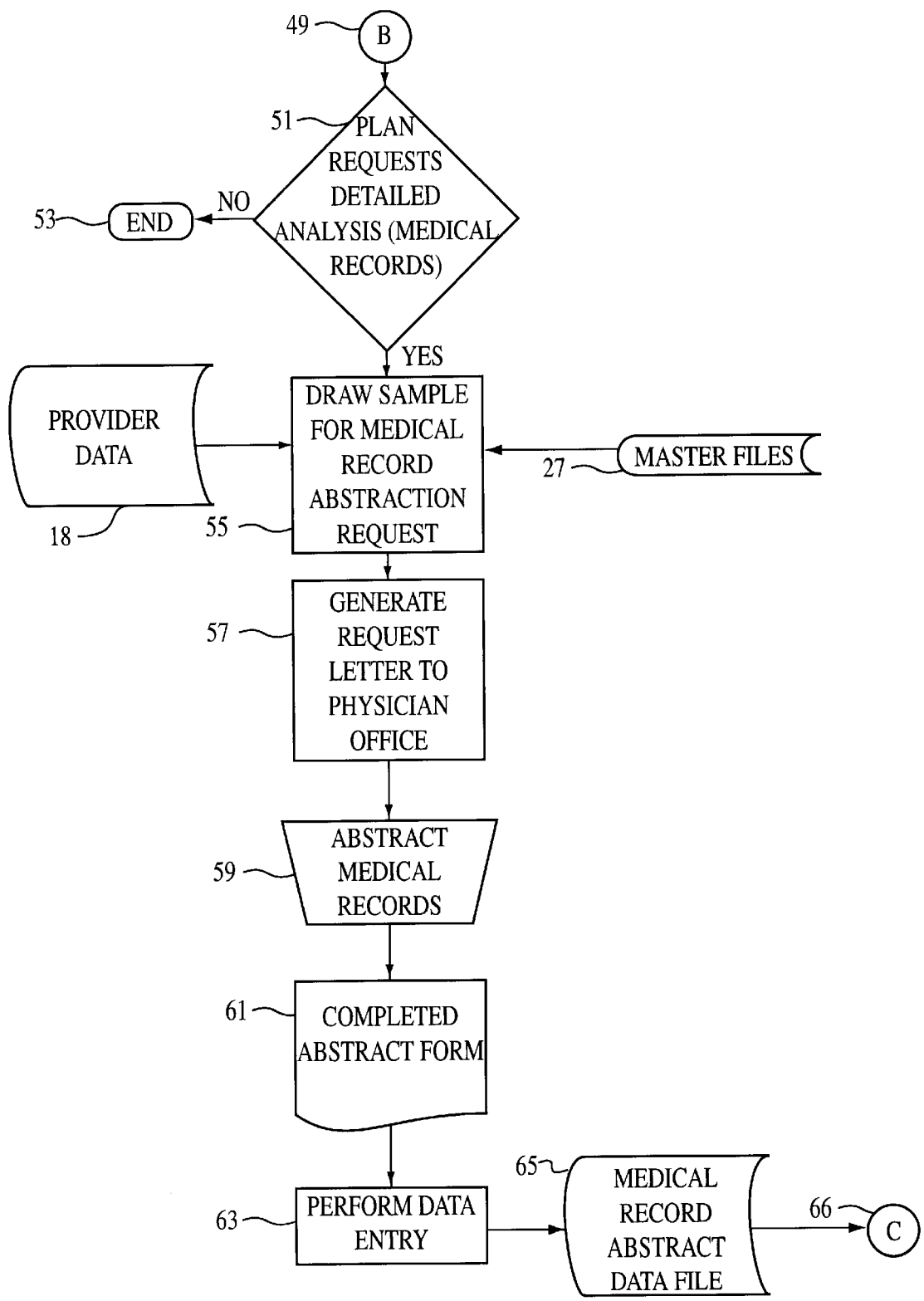
Figure 1D:
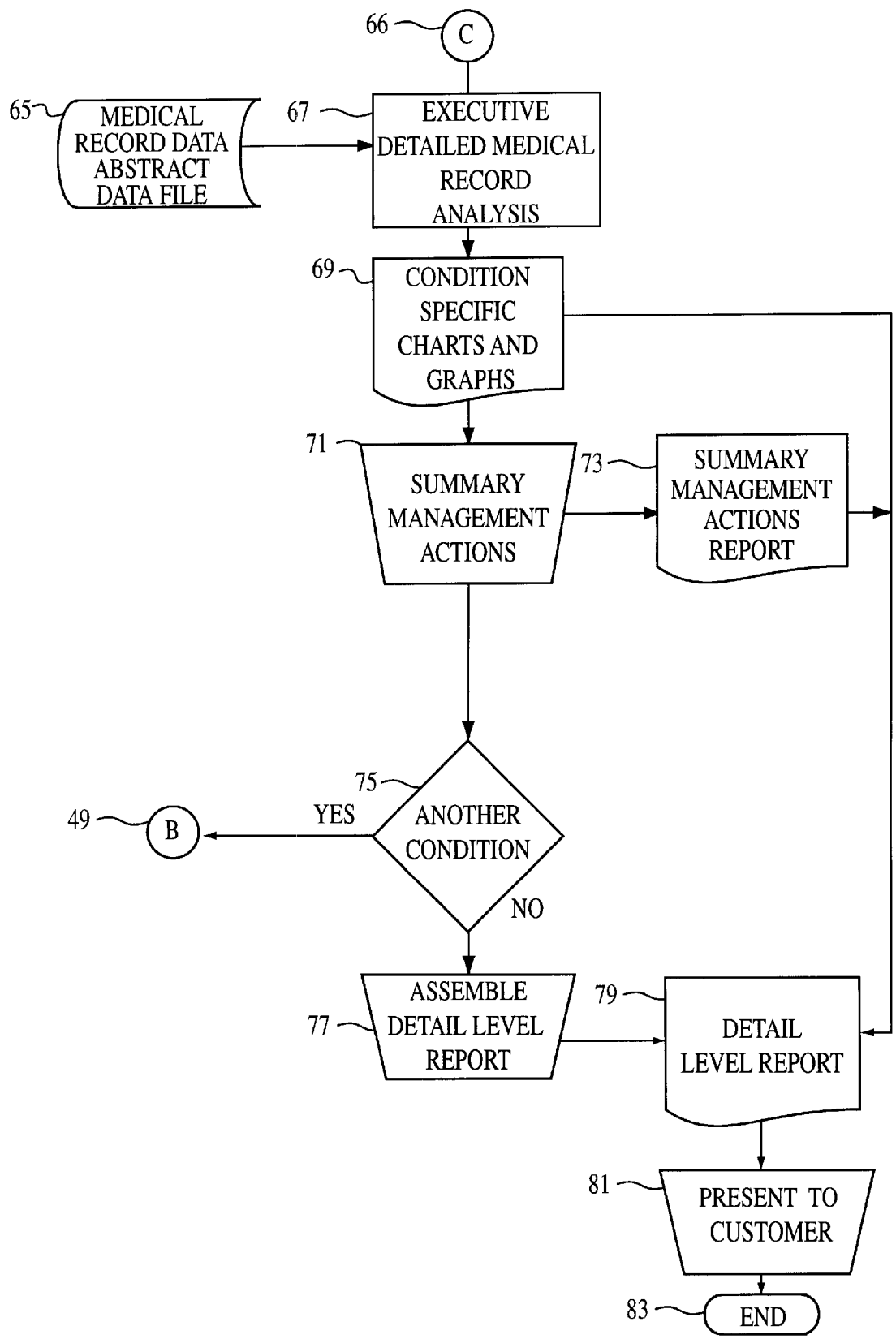
Figure 2:
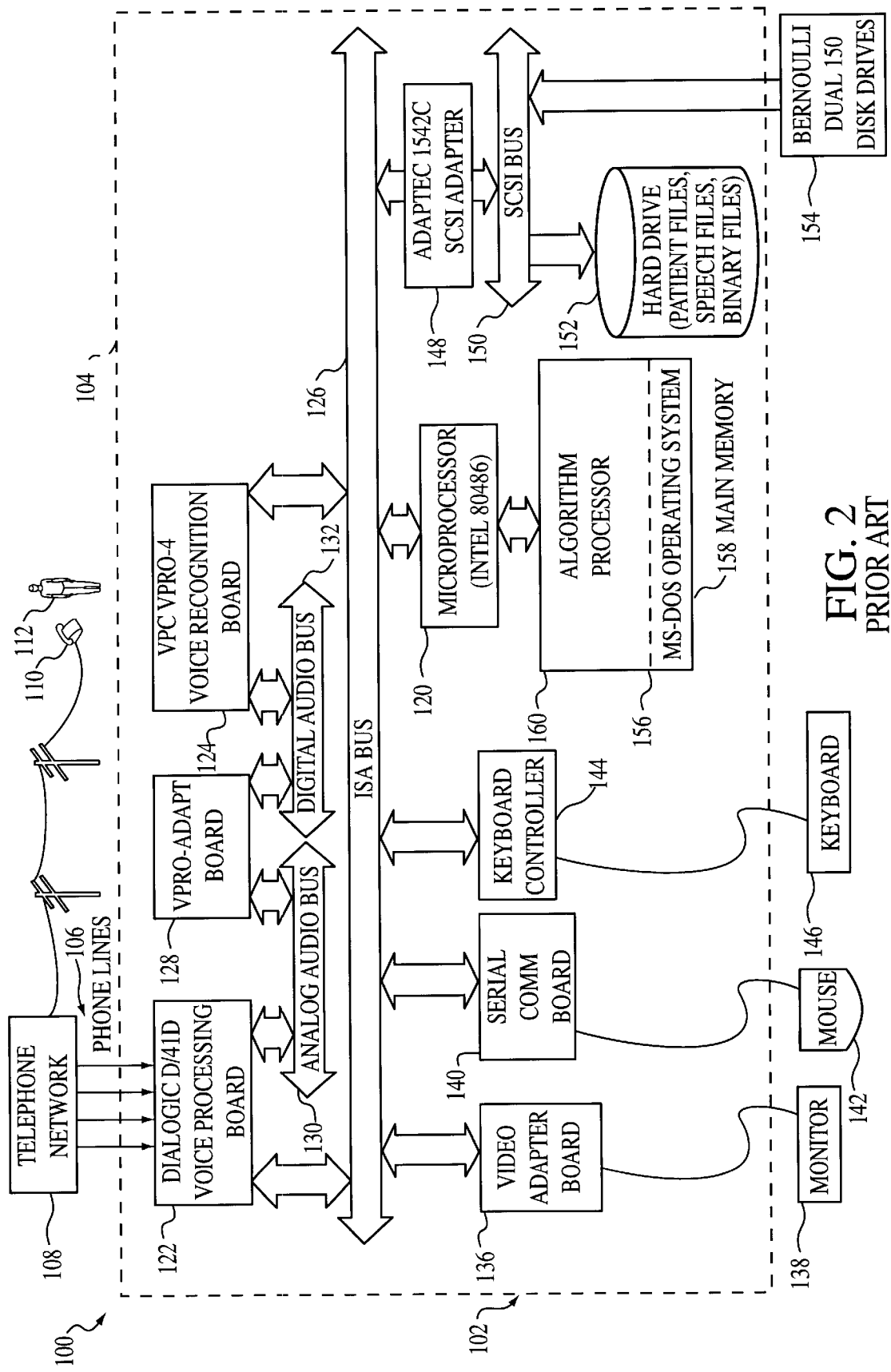
FIG. 2 is a block diagram illustrating the components of a presently preferred embodiment of the computerized medical diagnostic and treatment advice (MDATA) system of the present invention.
Figure 3:
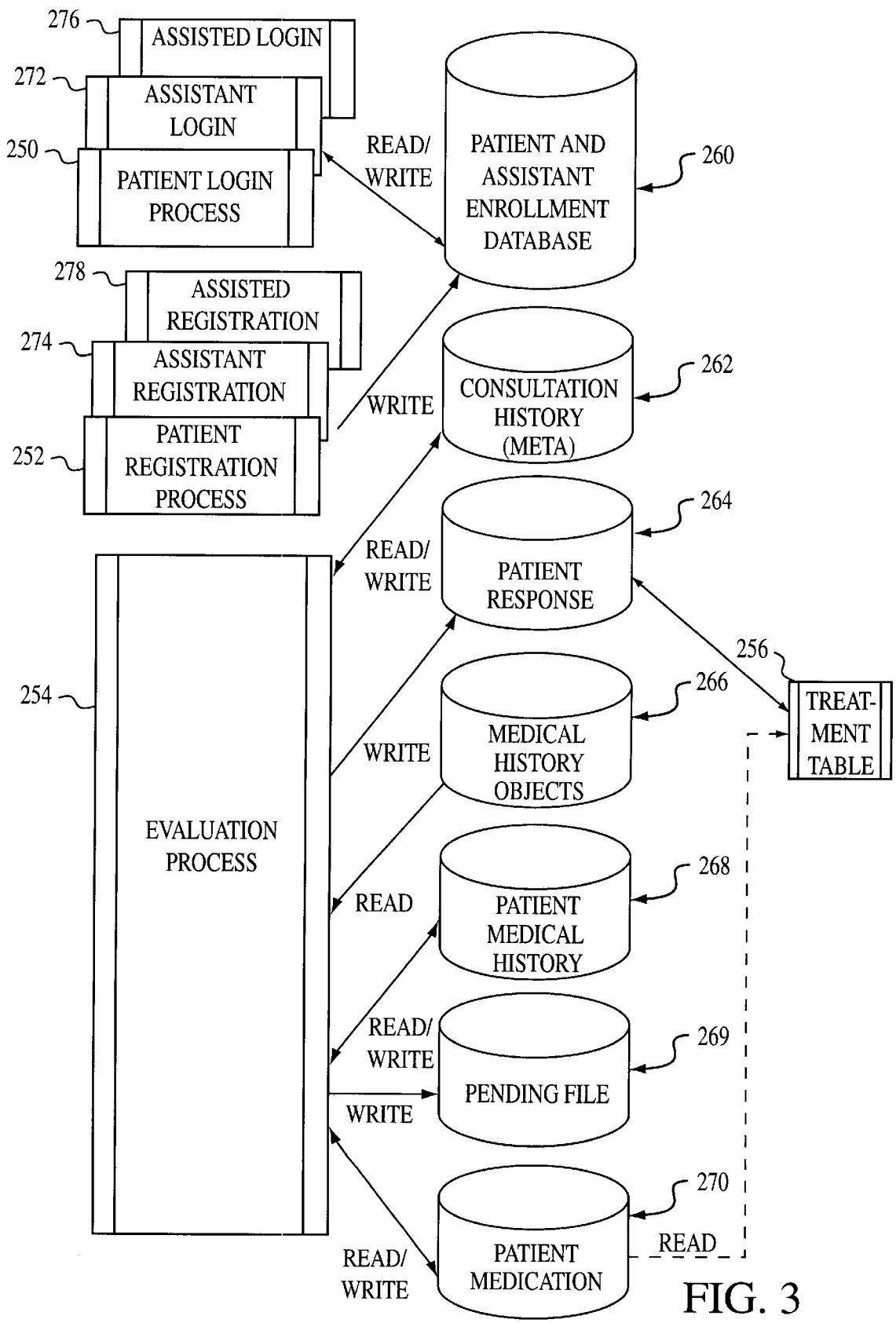
FIG. 3 is a block diagram illustrating a conceptual view of the database files and processes of the system of FIG. 2.
Figure 4:
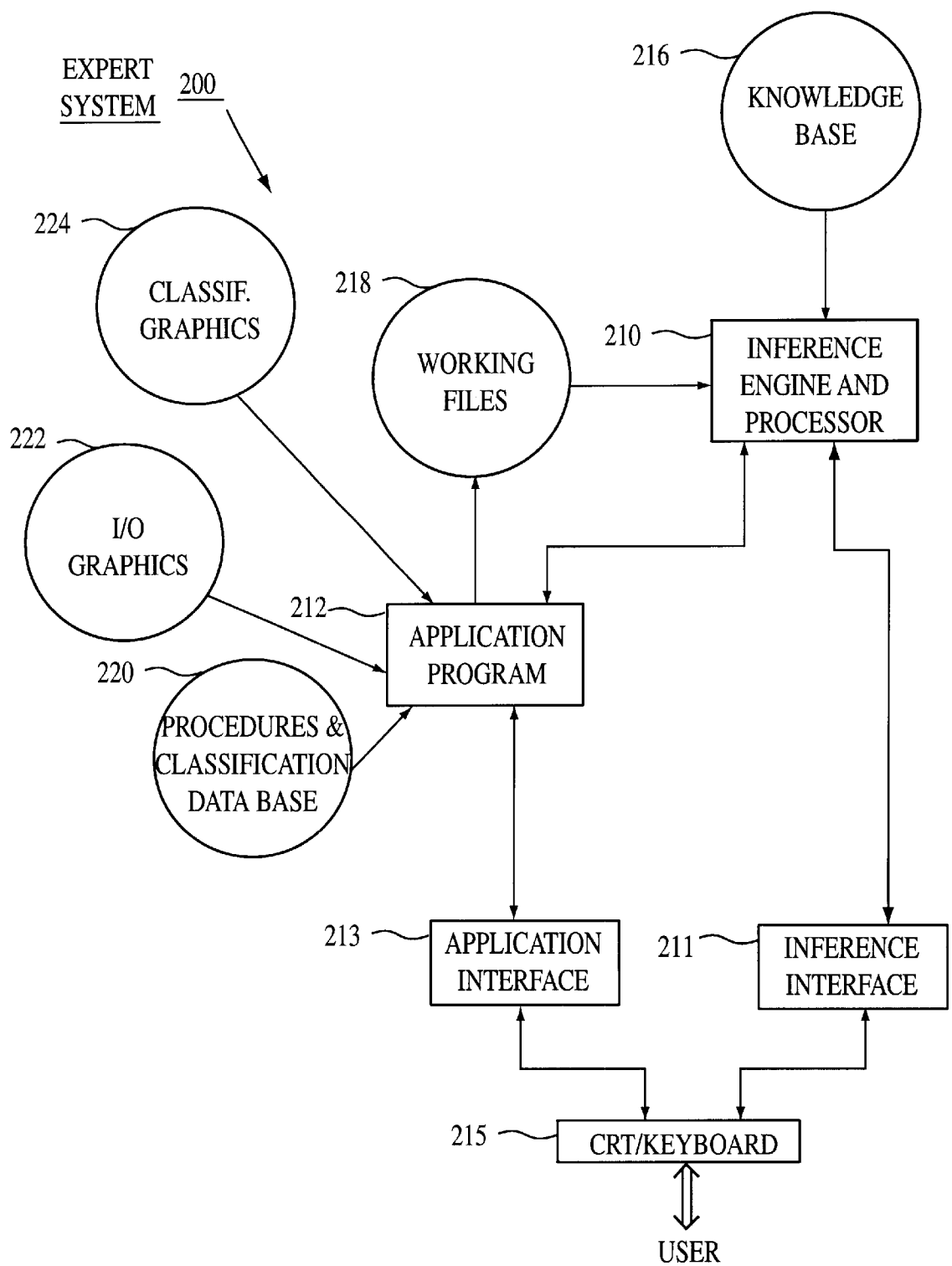
FIG. 4 is a block diagram illustrating the structure of an expert system for suggesting treatments for physical trauma.

The detailed descriptions which follow may be presented in terms of program procedures executed on a computer or network of computers. These procedural descriptions and representations are the means used by those skilled in the art to most effectively convey the substance of their work to others skilled in the art.

A procedure is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention include general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

DESCRIPTION OF THE PREFERRED EMBODIMENT OF THE INVENTION

The patient medication and/or health care review of the present invention (hereinafter patient medication review or patient review) is a computer assisted and/or implemented program designed to gather the therapeutic history of patients, optionally over the telephone. The review provides, for example, a complete history of medication use, adverse effects, treatment goals, medical history, and patient concerns and satisfaction. The program integrally involves the patient's physician to verify current medications, discuss potential interventions and discuss any compliance issues.

The patient medication review goals are to improve or maintain patient care, while controlling or reducing drug spending, and increasing patient involvement in medication discussions. This patient review process ensures appropriate patient care through the collection of extensive information on a patient's use of, for example, the medication(s), medical history, and satisfaction, as well as the involvement of both the patient and physician in the decision-making process.

For purposes of the present invention "health care condition" is broadly defined to mean a condition in the nature of a disease or an organic dysfunction or a "condition" that might also be viewed as a status or an outcome.

Advantageously, the process and/or system of the present invention is optionally used in connection with a mail service pharmacy. In addition, the present invention includes contact (e.g., in-person, telephone, computer, facsimile, e-mail, Internet, web site, and the like) with the patient's physician as a unique component of the program. The review program is designed to gather the therapeutic history of patients over the telephone. The benefits of the present invention include significantly improving or maintaining patient care while controlling or reducing drug spending, and increasing patient involvement in medication discussions. Enrolled patients are called and a patient medication profile is created, including information on: patient demographics, patient's physician(s), current medications, medication use pattern, OTC medication use, patient understanding of treatment goals, adverse effects, compliance history, medical/family history, hospitalization history, pertinent laboratory work, patient concerns and assessment, and patient satisfaction assessment.

Analysis of these and other data are conducted to evaluate various drug related problems. The present invention also optionally (1) integrates over-the-counter medication use, (2) incorporates patient-reported medication issues, (3) evaluates compliance and refill history, and/or (4) optimizes and/or coordinates patient therapy. A unique aspect of this program is that the patient's physician is contacted (via, for example, a telephone, computer automatically, e-mail, facsimile, and the like) to, for example, verify current medications, discuss potential interventions, establish therapeutic goals, verify adverse drug reactions, and discuss any compliance issues.

Figure 5:
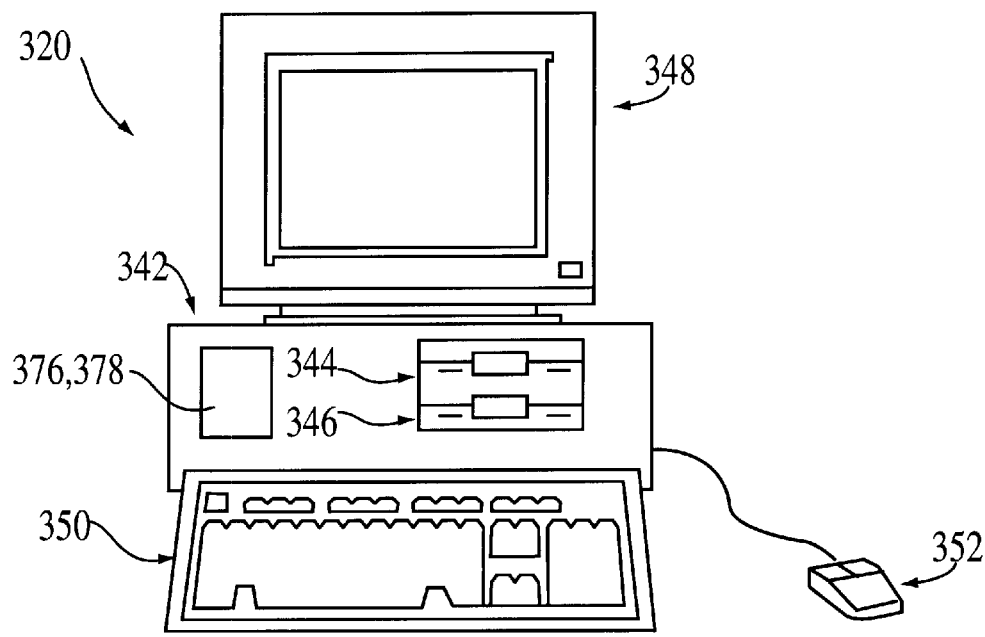
FIG. 5 is an illustration of a computer of a type suitable for implementing and/or assisting in the implementation of the processes described herein.

The final steps in the program include a summary letter sent to physician, a summary of therapy changes sent to patient, a call from a pharmacist to the patient, and a health status survey (SF-12) sent to the patient. Examples of drug related problems include, but not limited to:

Untreated indication
   includes therapeutic failures
Drug use without an indication
Improper drug selection
   includes therapeutic duplications
Improper dosage
Drug Interactions
   Drug-Drug, Drug-Food and Drug-Disease
Inadequate drug delivery
   includes non-compliance
Adverse drug reactions
Improper monitoring FIG. 5 illustrates a computer of a type suitable for carrying out the invention. Viewed externally in FIG. 5, a computer system designated by reference numerals 320, 326, 332 and/or 340 has a central processing unit 342 having disk drives 344 and 346. Disk drive indications 344 and 346 are merely symbolic of a number of disk drives which might be accommodated by the computer system. Typically these would include a floppy disk drive such as 344, a hard disk drive (not shown externally) and a CD ROM indicated by slot 346. The number and type of drives varies, typically with different computer configurations. Disk drives 344 and 346 are in fact optional, and for space considerations, may easily be omitted from the computer system used in conjunction with the processes described herein.

The computer also has an optional display 348 upon which information is displayed. In some situations, a keyboard 350 and a mouse 352 may be provided as input devices to interface with the central processing unit 342. Then again, for enhanced portability, the keyboard 350 may be either a limited function keyboard or omitted in its entirety. In addition, mouse 352 may be a touch pad control device, or a track ball device, or even omitted in its entirety as well.

Figure 6:
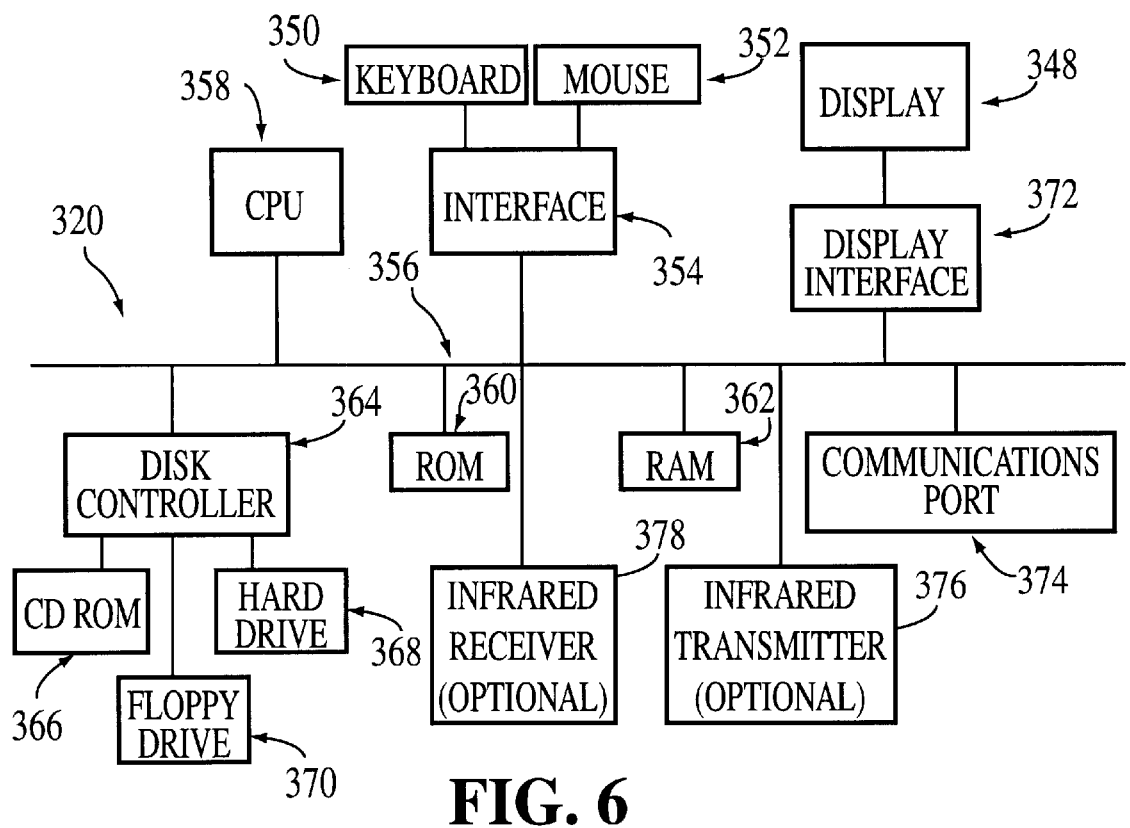
FIG. 6 is a diagram of the internal hardware of the computer illustrated in FIG. 5 in accordance with a first embodiment.

In addition, the computer system also optionally includes at least one infrared transmitter 376 and/or infrared receiver 378 for either transmitting and/or receiving infrared signals. FIG. 6 illustrates a block diagram of the internal hardware of the computer of FIG. 5. A bus 356 serves as the main information highway interconnecting the other components of the computer. CPU 358 is the central processing unit of the system, performing calculations and logic operations required to execute a program. Read only memory (ROM) 360 and random access memory (RAM) 362 constitute the main memory of the computer. Disk controller 364 interfaces one or more disk drives to the system bus 356. These disk drives may be floppy disk drives such as 370, or CD ROM or DVD (digital video disks) drive such as 366, or internal or external hard drives 368.

As indicated previously, these various disk drives and disk controllers are optional devices. A display interface 372 interfaces display 348 and permits information from the bus 356 to be displayed on the display 348. Again as indicated, display 348 is also an optional accessory. For example, display 348 could be substituted or omitted from the device, and a display on the telephone may be used to display information. Communication with external devices occurs utilizing communication port 374.

In addition to the standard components of the computer, the computer also includes at least one of infrared transmitter 376 or infrared receiver 378. Infrared transmitter 376 is utilized when the computer system is used in the process described herein. Infrared receiver 378 is generally utilized when the computer system is used in conjunction with the telephone that is to receive the infrared signal.

Figure 7:
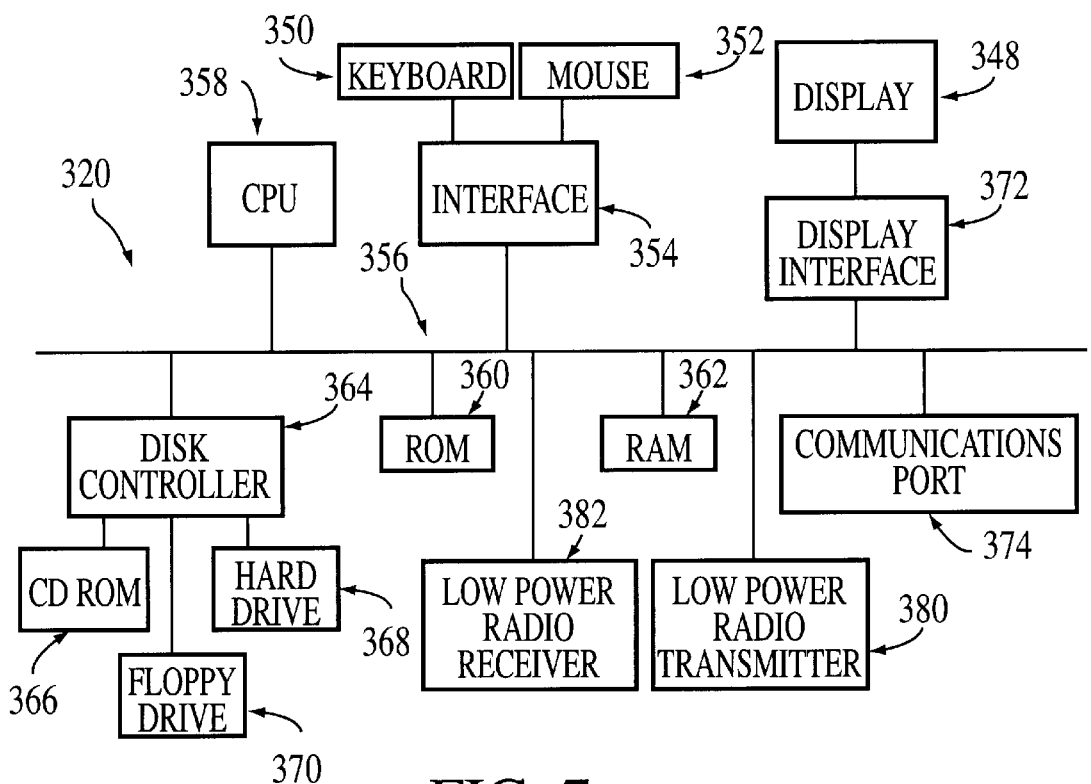
FIG. 7 is a block diagram of the internal hardware of the computer of FIG. 5 in accordance with a second embodiment.

FIG. 7 is a block diagram of the internal hardware of the computer of FIG. 5 in accordance with a second embodiment. In FIG. 7, instead of utilizing an infrared transmitter or infrared receiver, the computer system uses at least one of a low power radio transmitter 380 and/or a low power radio receiver 382. The low power radio transmitter 380 transmits the signal for reception by the low power radio receiver 382. Once the low power radio receiver 382 receives the signal, the low power radio signal 382 transmits the signal. The low power radio transmitter and/or receiver 380, 382 are standard devices in industry.

Figure 8:
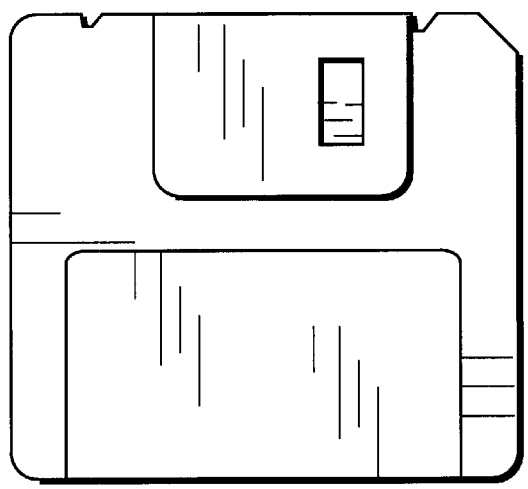
FIG. 8 is an illustration of an exemplary memory medium which can be used with the computer illustrated in FIGS. 5–7.

FIG. 8 is an illustration of an exemplary memory medium which can be used with disk drives illustrated in FIGS. 5–7. Typically, memory media such as floppy disks, or a CD ROM, or a digital video disk will contain, for example, a multi-byte locale for a single byte language and the program information for controlling the computer to enable the computer to perform the functions described herein. Alternatively, ROM 360 and/or RAM 362 illustrated in FIGS. 6–7 can also be used to store the program information that is used to instruct the central processing unit 358 to perform the operations associated with the present invention.

Figure 9:
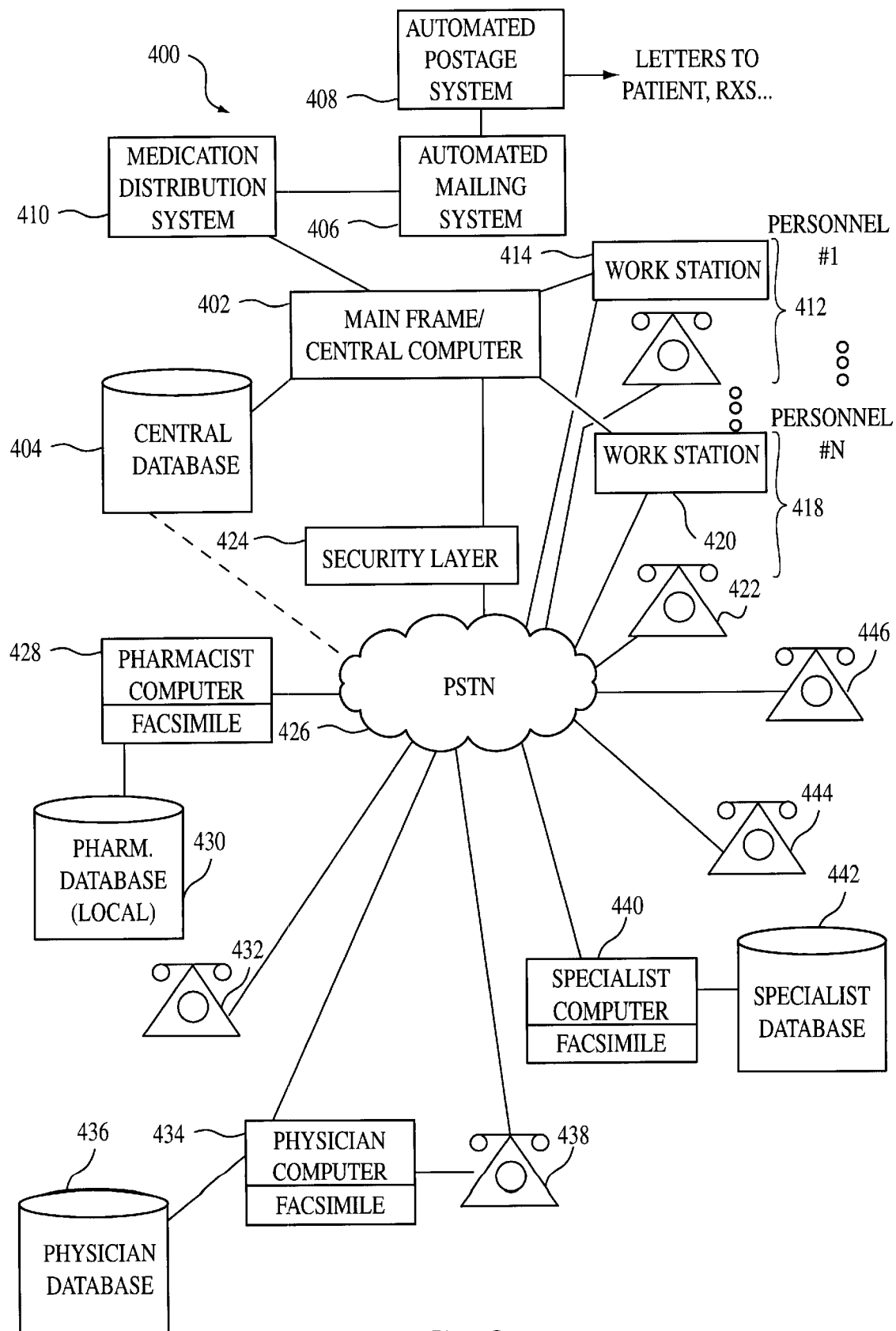
FIG. 9 is a block diagram of one embodiment of the hardware design of the present invention.

FIG. 9 is a block diagram of one embodiment of the hardware design of the present invention. In FIG. 9, medication review system 400 includes main frame or central computer 402 that controls or coordinates requests for receiving and/or storing patient related data, such as including information on: patient demographics, patient's physician(s), current medications, medication use pattern, over the counter (OTC) medication use, patient understanding of treatment goals, adverse effects, compliance history, medical/family history, hospitalization history, pertinent laboratory work, patient concerns and assessment, and patient satisfaction assessment in central database 404. Main frame 402 may optionally be a stand-alone personal computer (PC) that communicates with workstations in a standard manner, as needed.

Central computer 402 transmits data, such as letters to be mailed, to optional and standard automated mailing system 406. Optional automated mailing system 406 transmits the packages to optional and standard automated postage system outputs the letters, packages and the like. An optional medication distribution system 410 is also provided to dispense various medications in accordance with determinations made by the patient medication review system 400.

Multiple workstations and personnel are optionally provided. For example, work station personnel 412 utilizes workstation 414 and telephone 416 to interact with patients for contacting the patients and collecting data therefrom. In addition, work station personnel 418 utilizes workstation 420 and telephone 422 also to interact with patients for contacting the patients and collecting data therefrom. Any number of work stations may be used to contact patients and collect data. Workstation personnel interface with one or patients 446 via, for example, public switched telephone network (PSTN) 426. Other types of communications networks may be used, such as local area networks, Internet, coaxial cable systems, wireless, and the like.

In addition to contacting the patients 446, work station personnel optionally connect to and/or conference in pharmacist computer 428 to obtain, for example, current medication information on the patient stored in database 430, and also to speak with a pharmacist regarding the patient. When the medication information is to be changed, the pharmacist is also contacted either via telephone 432 or computer 428 including an optional facsimile modem.

Work station personnel optionally connect to and/or conference in physician computer 434 to obtain, for example, current health information on the patient optionally stored in database 436, and also to speak with a physician regarding the patient via telephone 438. When the medication information is to be changed, the physician contacts the pharmacist for the change, either via telephone 438 or computer 434 including an optional facsimile modem. Thus, the physician may transmit the change in medication either orally or via data transmission, such a facsimile, direct or indirect computer links, and the like.

Work station personnel optionally connect to and/or conference in a physician specialist via telephone 442 to obtain, for example, additional information with respect to more complicated patient conditions. The specialist may also optionally consult database 442 via computer 440 to obtain additional information. When the medication information is to be changed, the specialist contacts the pharmacist for the change, either via telephone 444 or computer 440 including an optional facsimile modem. Thus, the specialist may transmit the change in medication either orally or via data transmission, such a facsimile, direct or indirect computer links, and the like.

An optional connection from central database 404 to PSTN 426 is also provided. Central database 404 may optionally comprise a plurality of databases that collectively store the appropriate patient information described above. An optional security layer 424 is also provided to prevent unauthorized access to central computer 402. Security layer 424 comprises any standard security scheme or technology, and may be used system wide as well, for example, with all workstations, pharmacist, physicians, and the like. As described above, the present invention does not require the direct interaction with the various computers, but provides this additional feature to further facilitate the communication process between various work station personnel, physicians, pharmacists, and the like.

Figure 10:
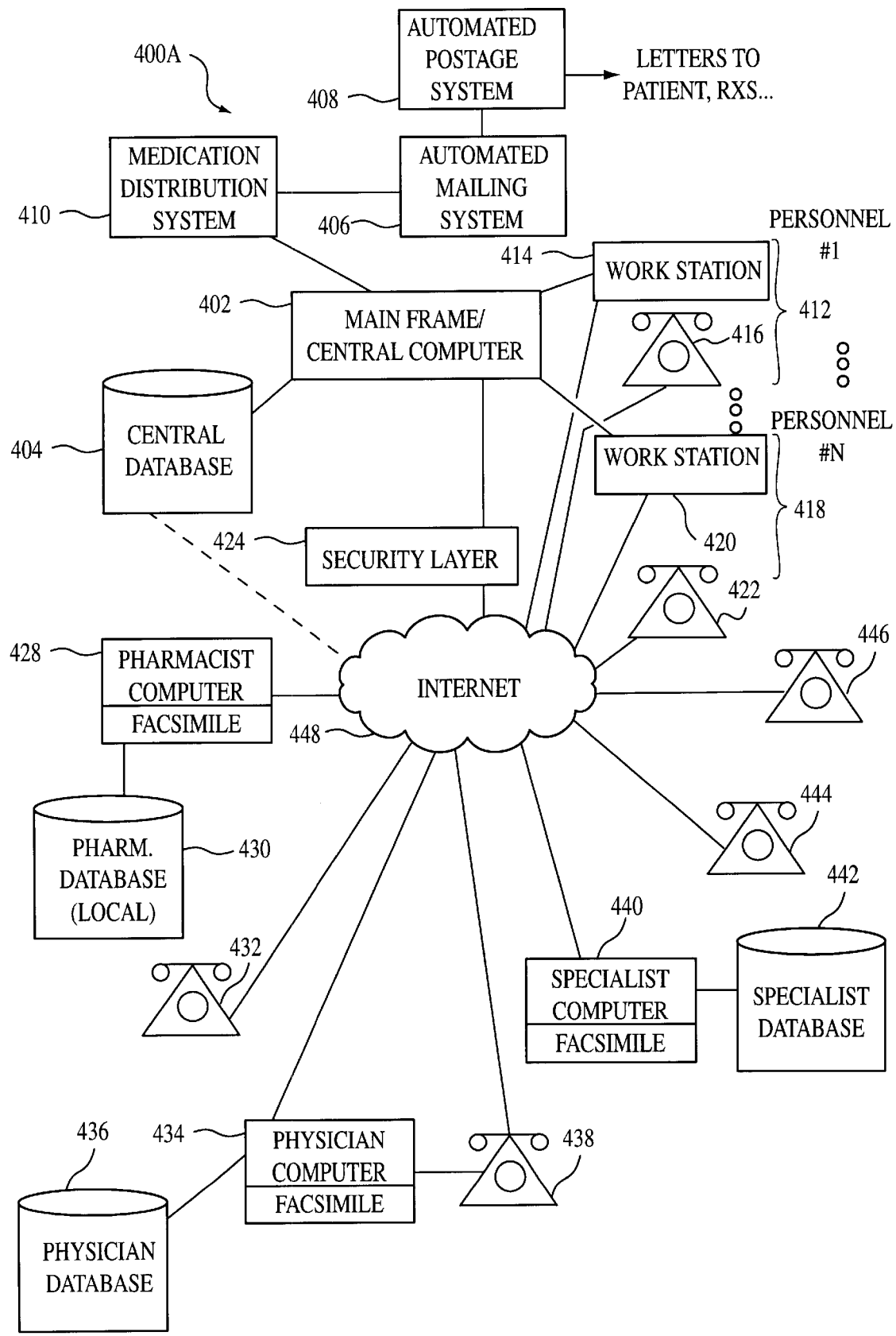
FIG. 10 is a block diagram of a second embodiment of the hardware design of the present invention.

FIG. 10 is a block diagram of a second embodiment of the hardware design of the present invention. In FIG. 10, the medication review system 400a includes main frame or central computer 402 that controls or coordinates requests for receiving and/or storing patient related data. In this embodiment of the invention, Internet network 448 is used as the main communications network between workstation personnel 412, 418 with one or patients 446, one or more pharmacists 432, one or more physicians 438, and/or one or more specialists 444. In addition, Internet network 448 is used as the main communications network between workstation computers 414, 420, one or more pharmacist computers 428, one or more physician computers 434, and/or one or more specialist computers 440. In this embodiment, security layer 424 is principally to prevent unauthorized intrusion into central computer 402 and central database 404.

Figure 11:
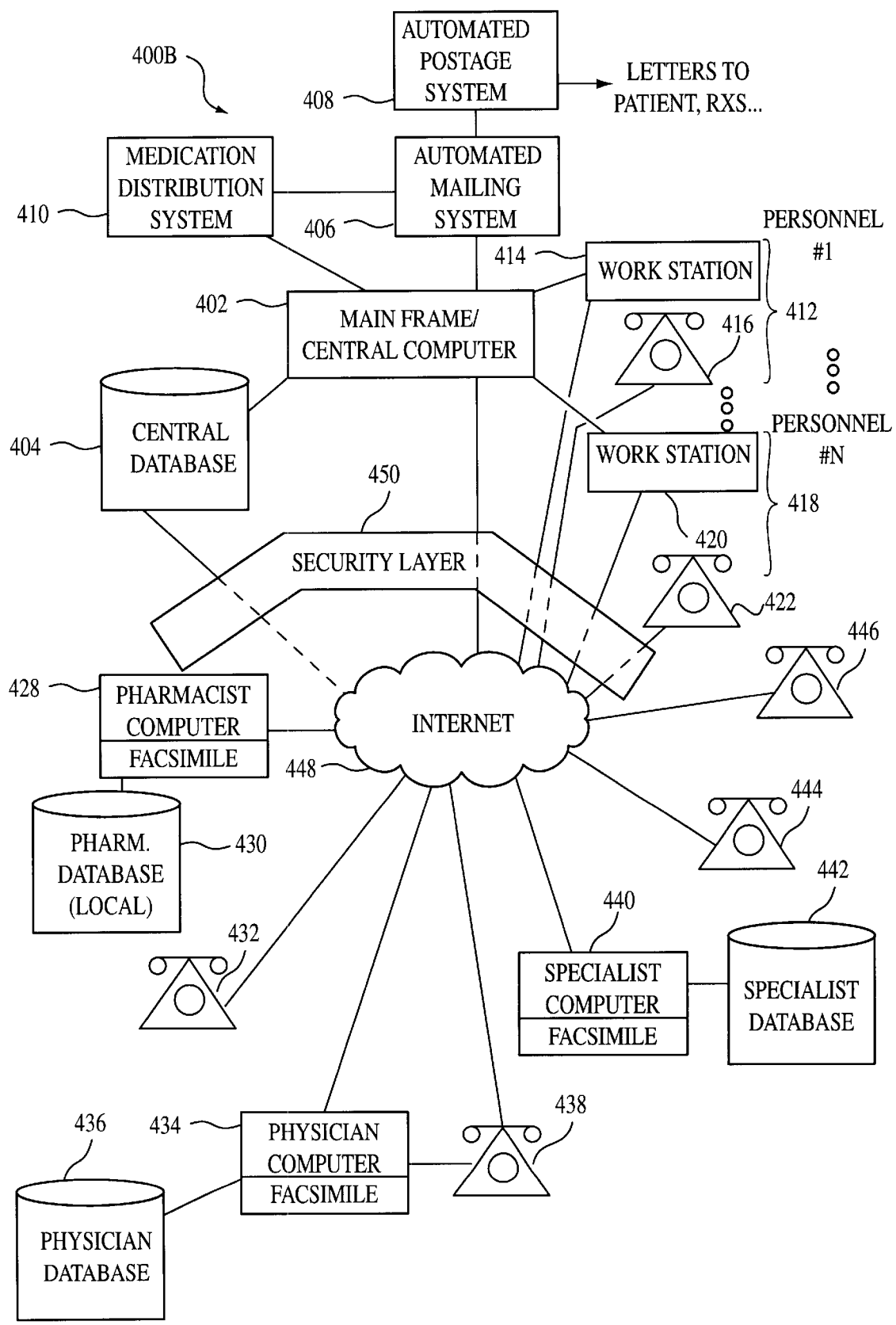
FIG. 11 is a block diagram of a third embodiment of the hardware design of the present invention.

FIG. 11 is a block diagram of a third embodiment of the hardware design of the present invention. In FIG. 11, the medication review system 400b includes main frame or central computer 402 that controls or coordinates requests for receiving and/or storing patient related data. In this embodiment of the invention, Internet network 448 is used as the main communications network between workstation personnel 412, 418 with one or patients 446, one or more pharmacists 432, one or more physicians 438, and/or one or more specialists 444. In addition, Internet network 448 is used as the main communications network between workstation computers 414, 420, one or more pharmacist computers 428, one or more physician computers 434, and/or one or more specialist computers 440. Security layer 450 is expanded and used to prevent unauthorized intrusion into central computer 402, central database 404 and workstations 414, 420 and personnel 412, 418.

Figure 12:
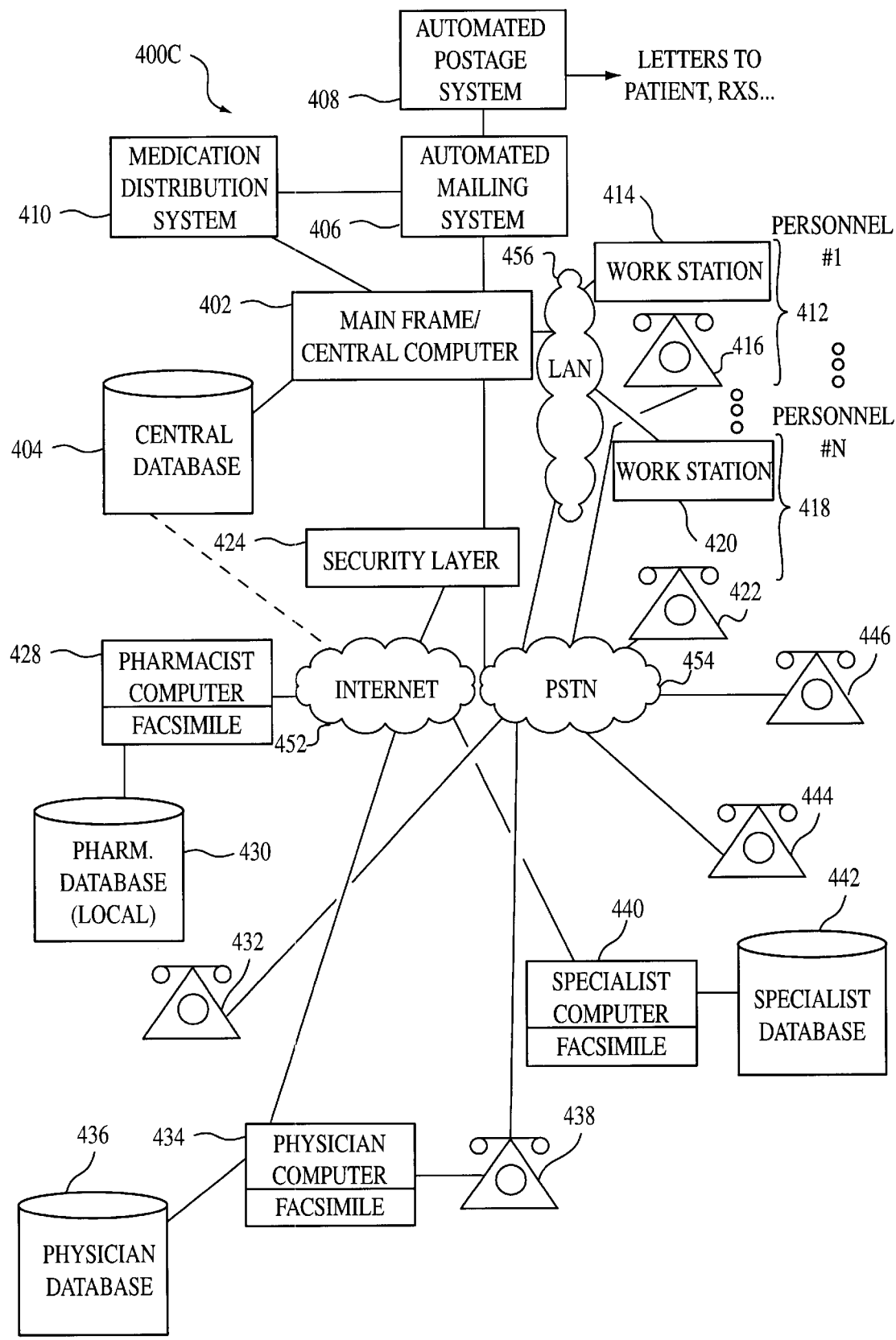
FIG. 12 is a block diagram of a fourth embodiment of the hardware design of the present invention.

FIG. 12 is a block diagram of a fourth embodiment of the hardware design of the present invention. In FIG. 12, the medication review system 400c includes main frame or central computer 402 that controls or coordinates requests for receiving and/or storing patient related data. In this embodiment of the invention, public switched telephone network 454 is used as the main communications network between workstation personnel 412, 418 with one or patients 446, one or more pharmacists 432, one or more physicians 438, and/or one or more specialists 444. In addition, Internet network 452 is used as the main communications network between workstation computers 414, 420, one or more pharmacist computers 428, one or more physician computers 434, and/or one or more specialist computers 440. Security layer 424 is used to prevent unauthorized intrusion into central computer 402, and central database 404. Workstation computers 414, 420 communicate with central computer 402 via an optional local area network 456.

Figure 13:
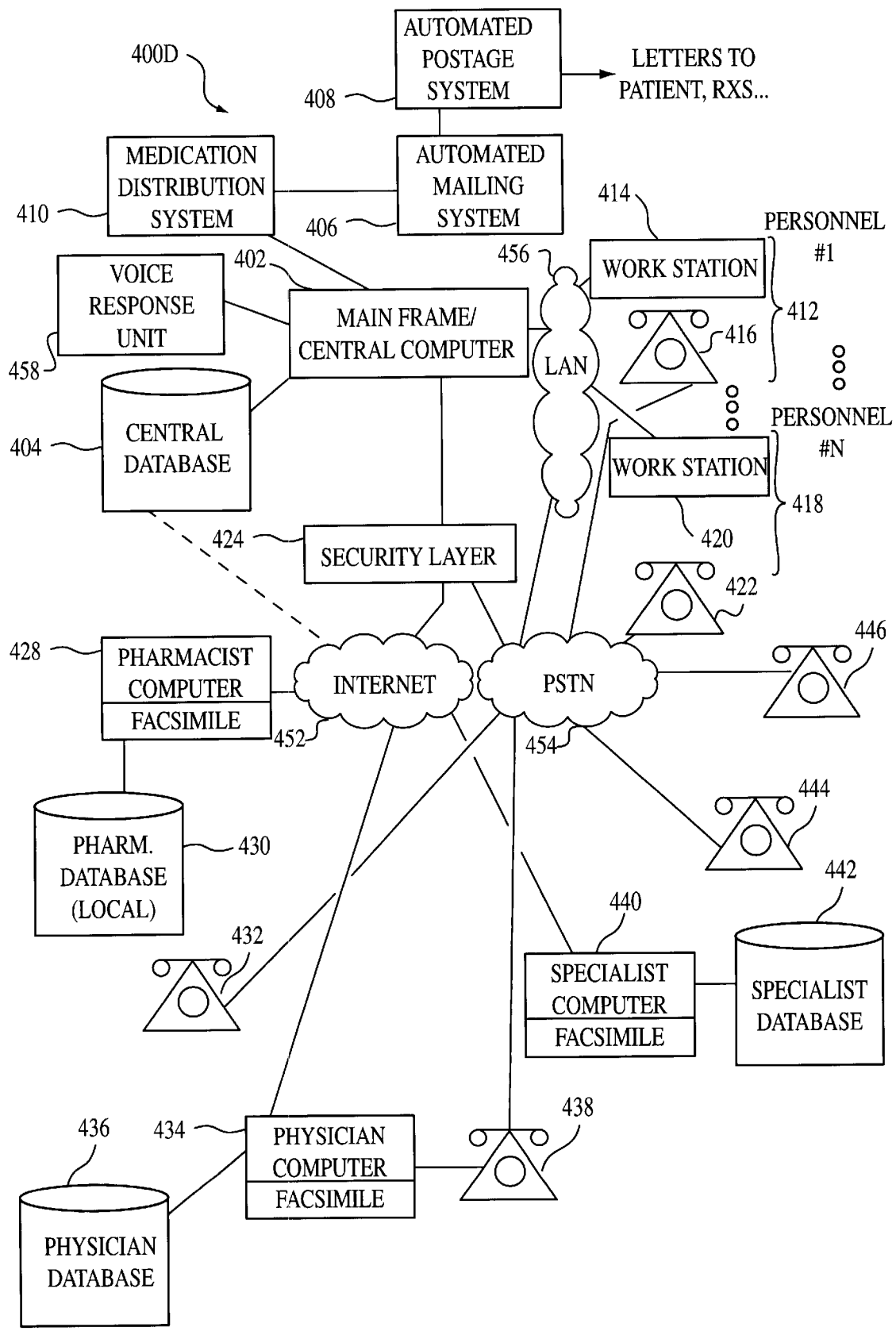
FIG. 13 is a block diagram of a fifth embodiment of the hardware design of the present invention.

FIG. 13 is a block diagram of a fifth embodiment of the hardware design of the present invention. In FIG. 13, the medication review system 400d includes main frame or central computer 402 that controls or coordinates requests for receiving and/or storing patient related data. In this embodiment of the invention, public switched telephone network 454 is used as the main communications network between workstation personnel 412, 418 with one or patients 446, one or more pharmacists 432, one or more physicians 438, and/or one or more specialists 444. In addition, Internet network 452 is used as the main communications network between workstation computers 414, 420, one or more pharmacist computers 428, one or more physician computers 434, and/or one or more specialist computers 440.

Security layer 424 is used to prevent unauthorized intrusion into central computer 402, and central database 404. Workstation computers 414, 420 communicate with central computer 402 via an optional local area network 456. An optional voice response unit 458 is also included to provide mechanized delivery of voice messages. This optional voice response unit 458 may also be utilized in any of the embodiments of the present invention. Optional voice response unit 458 is operative in response to, for example, predetermined messages or questions to be provided to the patient, pharmacist, and/or physician. Voice response unit 458 is also designed to replace any of the above procedures implemented by the caller of the system, in accordance with standard programming techniques.

The computer assisted and/or implemented process aims to control drug spending while improving and/or maintaining the quality of care in an opportunity-rich patient population, generally having multiple medications for treating of one or more diseases. Cost reduction, where appropriate, safe, and effective, is a major objective and advantage of the present invention. The entire computer implemented and/or assisted process is centered around the patient's best interest and welfare, and some recommendations may however, in some instances, lead initially to increased cost to both the plan and the patient. The accent on the patient's best interest is likely to improve health outcomes and to reduce total health-care expenditures for both the patient and the plan.

Figure 14:
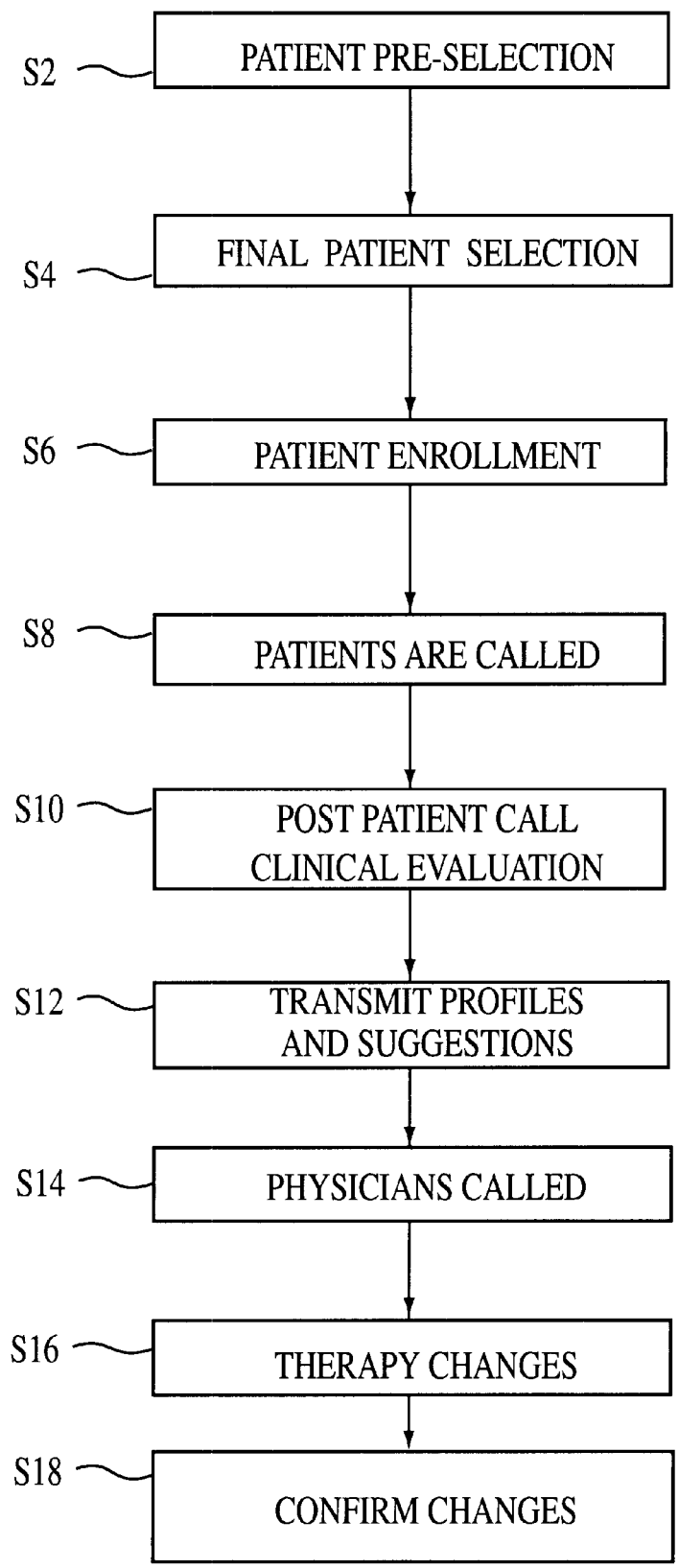
FIG. 14 is a conceptual flow chart of the computer assisted and/or implemented process of the present invention.
Figure 15:
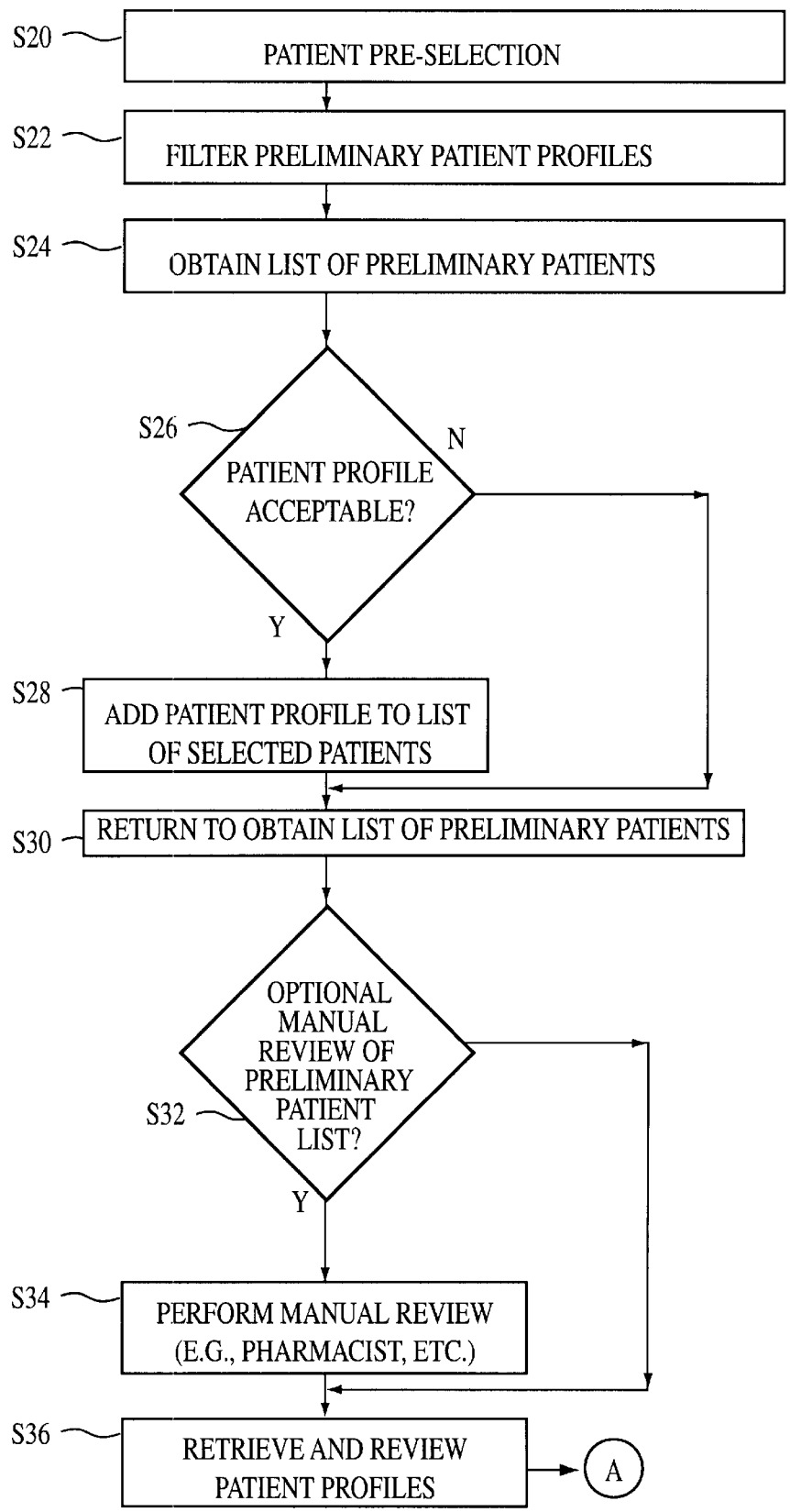
FIGS. 15–19 are flow charts of the computer assisted and/or implemented process of the present invention.
Figure 16:
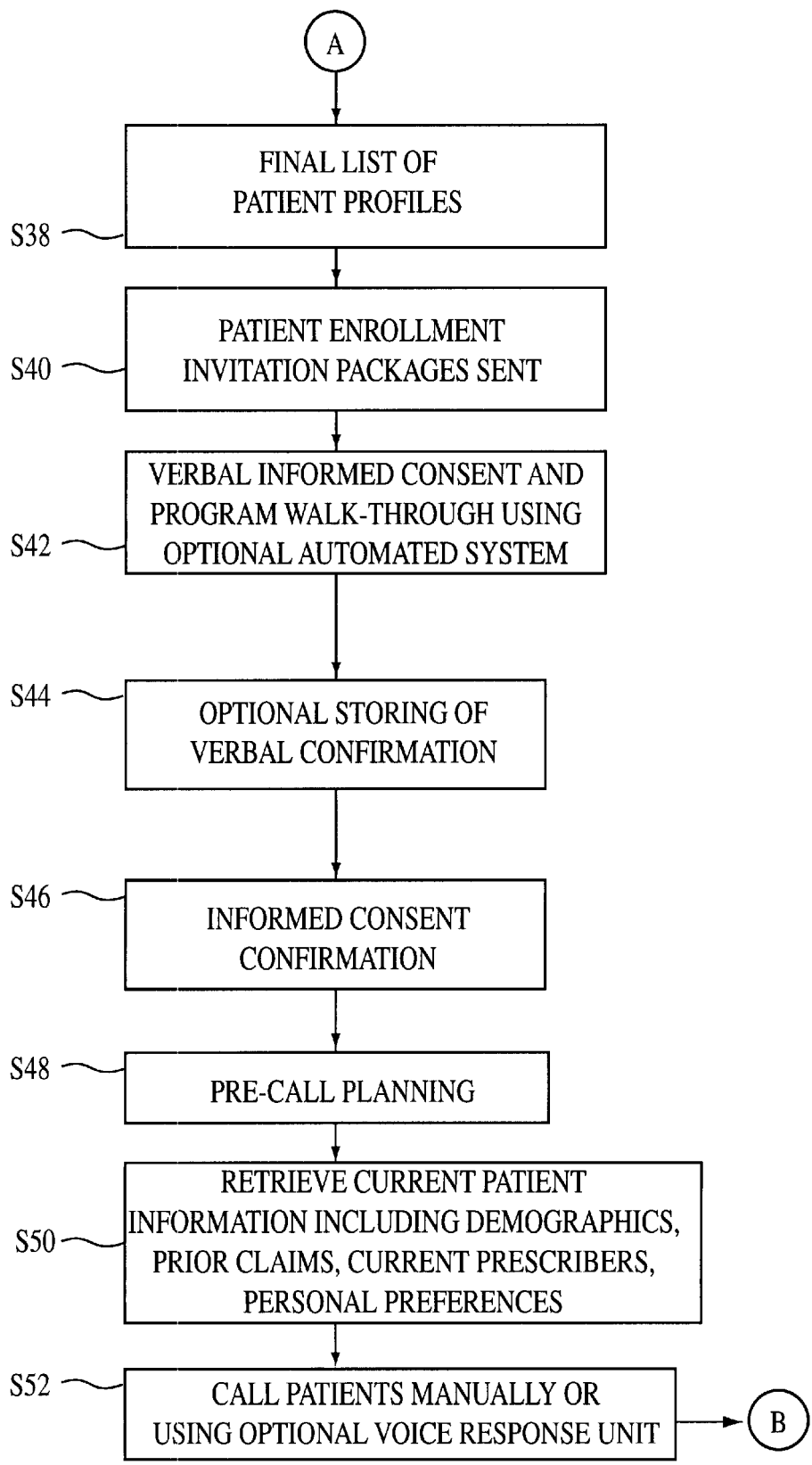
Figure 17:
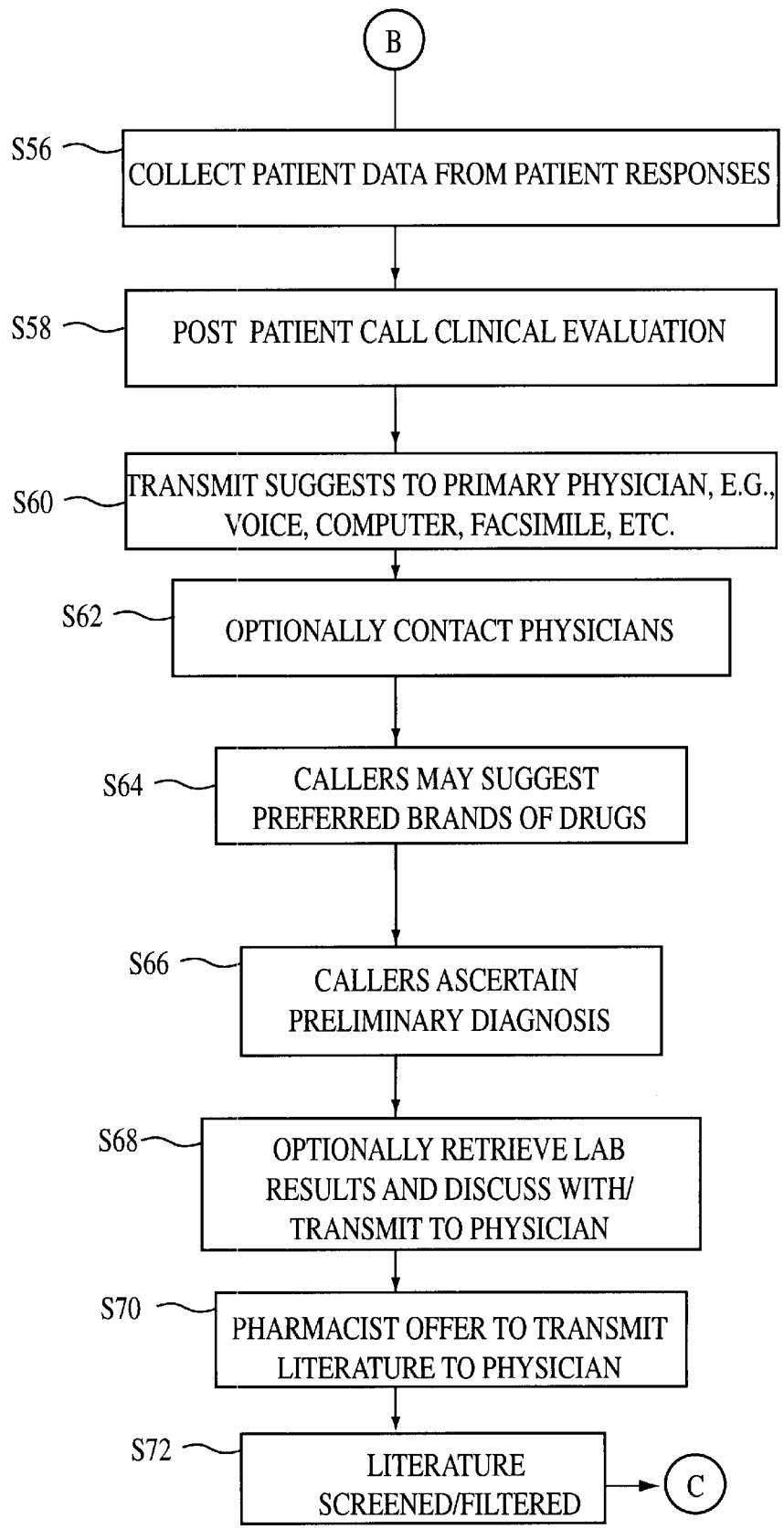
Figure 18:
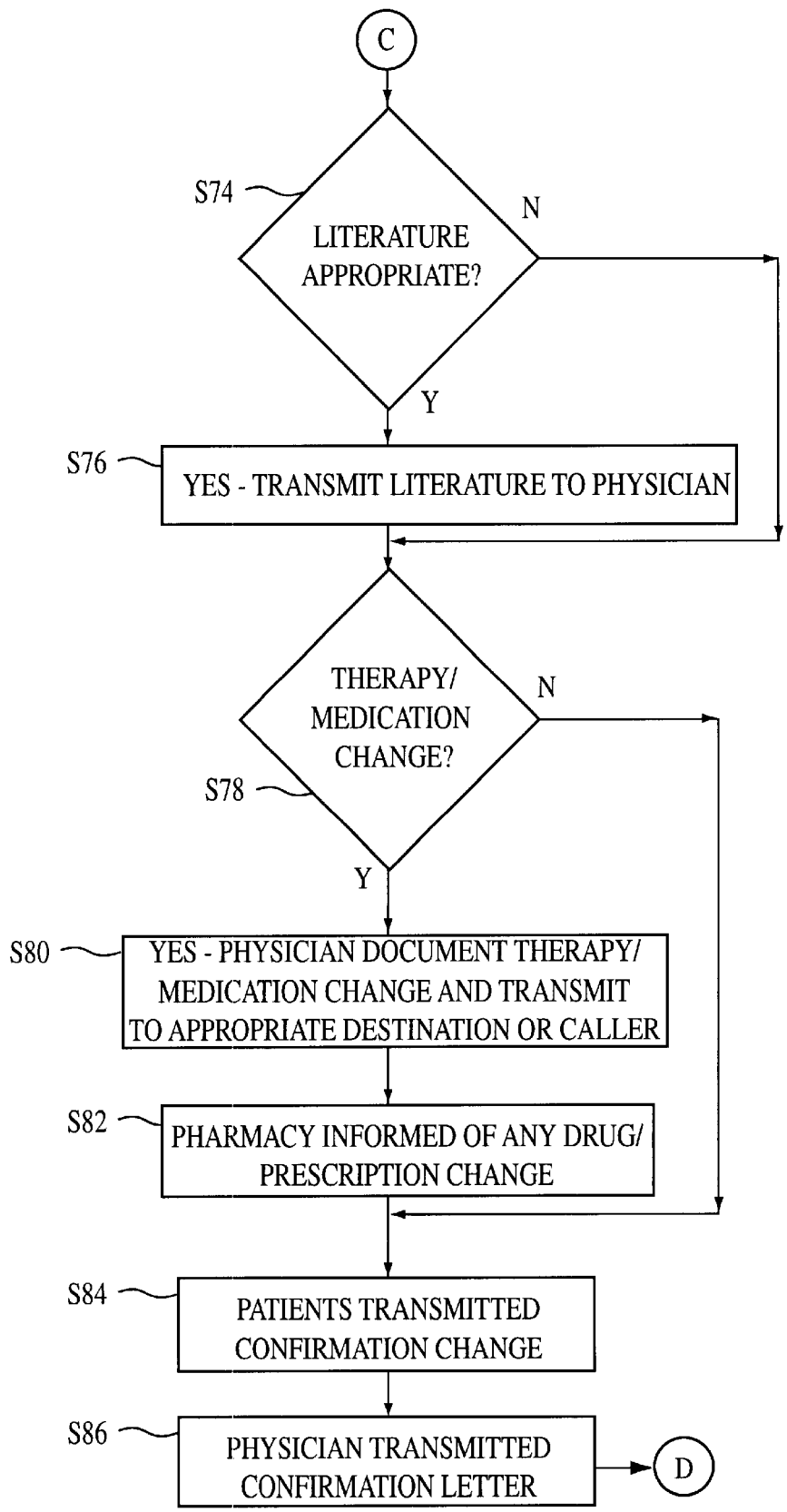
Figure 19:
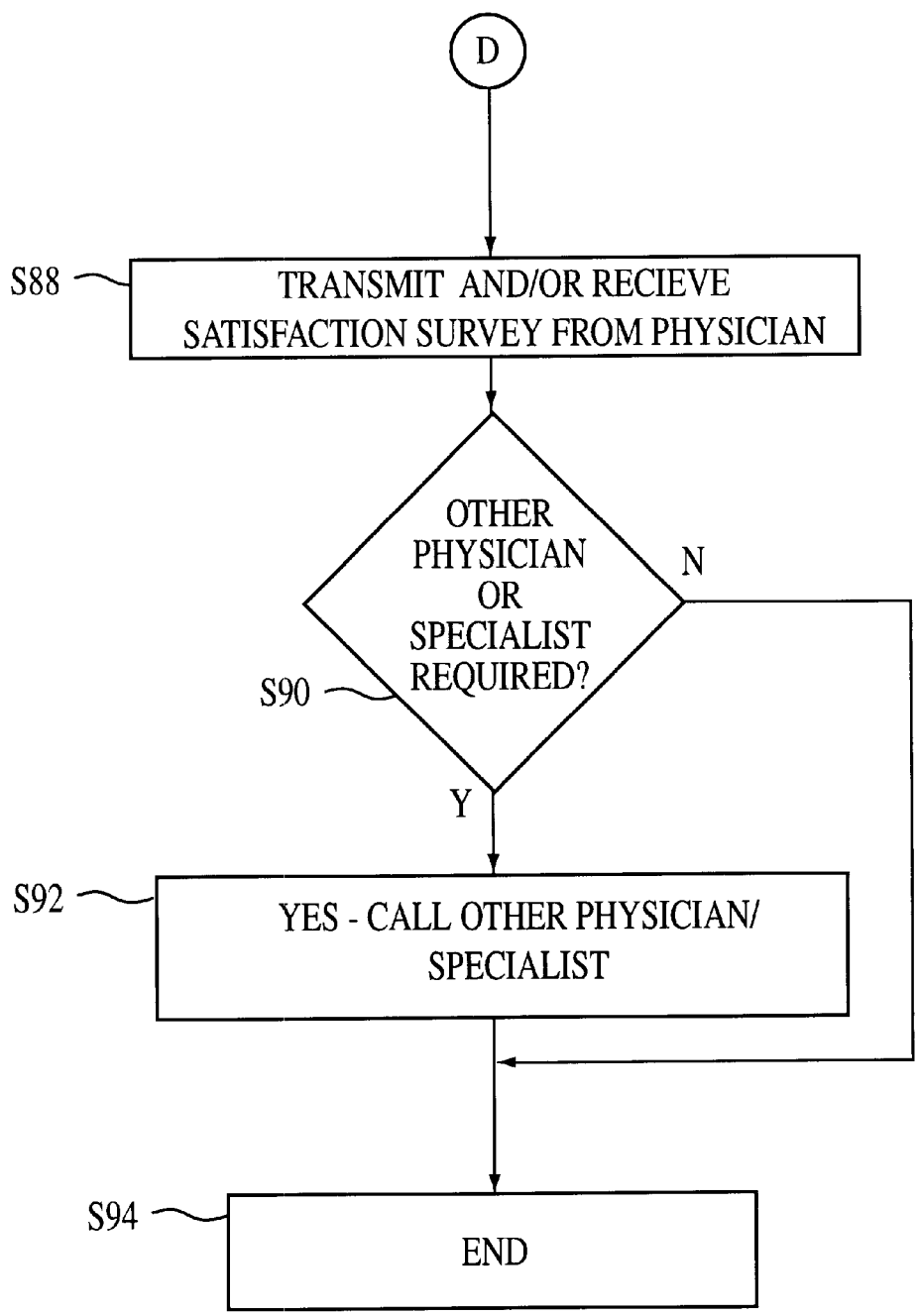

FIG. 14 is a conceptual flow chart of the computer assisted and/or implemented process of the present invention. In FIG. 14, patient pre-selection is performed in Step S2 to determine a first preliminary set of patients for which the computer assisted and/or implemented process is used. In Step S4, after various filtering is performed to identify a smaller set of patients that are most likely to benefit from the computer implemented and/or assisted process, final patient selection is performed.

In Step S6, patient enrollment is performed to obtain patient permission to interact with the computer implemented and/or assisted process. The enrollment step may be performed by an operator using the computer for assistance, or even entirely by the computer using, for example, a voice response unit. In Step S8, patients are called to obtain additional information from the patient to assist in the process of determining whether therapy and/or medication changes are appropriate.

In Step S10, the post patient call clinical evaluation process is conducted to determine whether therapy and/or medication changes are appropriate in view of data collected in step S8. In Step S12, the patient profiles and therapy/medication suggestions and/or considerations are transmitted to a reviewing physician. In Step S14, the physician is optionally called to discuss the proposed therapy/medication changes, and in Step S16, the proposed therapy/medication changes are implemented. In Step S18, the therapy/medication changed are optionally confirmed with the appropriate individuals, including, for example, the physician, patient, pharmacist, and the like.

FIGS. 15–19 are detailed flow charts of the computer assisted and/or implemented process of the present invention. In Step S20, patient pre-selection is performed, for example, retrospectively from medical claims in a disease management data base for adults only taking at least four maintenance medications and ranking in the top 3% of drug spenders over 18 years of age. Catastrophic patients with the following markers are optionally excluded or filtered in Step S22: AIDS, transplant, cancer, hemophilia, biotech. A patient list is generated in Step S24.

In Step S26, the process determines whether the patient profile is acceptable, and if so, the patient profile is added to the patient list in Step S28. In Step S30, the complete list of patients and patient profiles are compiled. In Step S32, the process determines whether an optional manual review of preliminary patient list is to be performed, and if so, in Step S34, the manual review is performed. In Step S36, the patient profiles are retrieved and reviewed. The profiles included in the patient pre-selection are updated with the latest claims available just prior to the physician calls, described below. The pharmacists also have access to the on-line mainframe and/or central database profiles, as described below in detail.

In Step S38, final patient selection is performed by the medication review system 400d and/or manually with the assistance of the medication review. system 400d. For example, one of the participating clinical pharmacists optionally pre-screens the profiles obtained from the computerized selection to eliminate false opportunities.

Patient enrollment invitation packages are optionally sent, in electronic and/or non-electronic format in Step S40, by the medication review system 400d and/or manually with the assistance of the medication review system 400d. In the enrollment package, patients are, for example, given an overview of the program and are asked to enroll by calling a toll free number or indicating a time when they should be called by the coordinator. The package also contains, for example, a "Record of Medications" which will be explained to them at the time of the first telephone contact. The invitations are generally sent out in staggered batches to avoid a glut of responses. Other methods of enrollment may also be used, such as by telephone contact and the like.

In Step S42, a verbal informed consent and program walk-through is performed, optionally using an automated system, such as the voice response unit described above. Customer service (1-800) pharmacists and/or coordinators, either receive an inbound call or make an outbound call according to the schedule received from the patient using the "Informed Consent" form, and explain the program thoroughly to the patient. Customer service personnel make the appropriate disclosures and obtain verbal informed consent. The verbal informed consent is optionally recorded in Step S44.

The customer service personnel then makes an appointment for a clinical professional to call the patient to discuss their medications and/or health care situation. An informed consent confirmation is transmitted to the patient in Step S46, for example, electronically or a letter is sent to patients who accept to participate.

In Step S48, pre-call planning is performed. Patient demographics and claims dating back to a predetermined date, other patient health related information, as well as information available about the patient's current prescribers, such as specialty and previously expressed desire not to be contacted on certain managed care programs, are retrieved and reviewed in Step S50.

Participating patients are called, either manually or using optional voice response unit, in Step S52. The callers will begin by introducing themselves and disclosing their affiliation with, for example, a particular company. If the calls are made by consultants, their affiliation statement will be "I am calling on behalf of Company XYZ." Callers collect the information provided by the patients from the "Record of Medications" and drill down for more clinical and lifestyle information in Step S56. Callers also, obtain the names and phone numbers of the primary doctor and other prescribers, and probe into the patient's disease states, and ask about their satisfaction with the program.

At the end of the call, the professional caller will, for example, ask for permission to call the patient's prescribers.

In Step S58, post patient call clinical evaluation is performed. The caller and an optionally assigned teammate will assess the information available and prepare a medication profile and a list of suggestions to be transmitted via, for example, facsimile, to the patient's primary doctor. Planning will include, inter alia, review of previous retro-drug utilization review (DUR) messages, if any, and enrollment in any disease management program to ensure coordination and continuity. The suggested changes will focus, inter alia, on dosing and duration reduction, elimination of unnecessary or harmful drugs, and therapeutic interchange. Suggestions leading to improved adherence will be made as necessary.

The majority of these issues will draw on existing concurrent or retro DUR protocols, prescribing guidelines, or other approved managed care and therapeutic management initiatives. Interventions concerning gastrointestinal (GI) and cardiovascular diseases are also optionally included. The conversations or questions posed/prompted to the patient includes significant drug problems. Interventions in this program will not generally be driven by brand or generic mix alone. Callers will generally discuss medications as complements to the main clinical message of better quality of living.

Once the appropriate suggestions have been formulated, the profiles and suggestions are transmitted to the physician in Step S60. The physician's office is contacted to obtain a secure fax number, if needed. An optional cover letter will accompany the profile. The fax will be followed by a call to secure a telephone appointment to discuss the materials faxed.

The physicians are optionally called in Step S62, either manually or using optional voice response unit, or a combination of both. In fact, any of the processes described herein that are performed manually or using the voice response unit may include a combination of both. The callers (e.g., voice response unit and/or individual) begin by introducing themselves and disclosing their affiliation with a company. Callers may optionally suggest preferred brands of medications in Step S64. As part of the program rationale, callers may reiterate or review the message sent to the patient.

Callers may ascertain preliminary diagnoses in step S66 for the conditions where recommendations seem relevant and/or appropriate from the profile review and patient conversations. Callers may also need to discuss lab test results such as cholesterol LDL/HDL levels, blood pressure measurments, levels, ejection fraction values, etc., as well as other information obtained from the patient as necessary, or optionally from labs and/or lab databases in Step S68.

Pharmacists may offer to and send literature in Step S70 from, for example, peer review journals if requested or accepted by the physician. The content of these materials will screened or filtered by, for example, clinical managers in Step S72. If the literature is determined to be appropriate in Step S74, the literature is transmitted in Step S76. The primary physician is asked to effect as many of the changes as possible or to obtain approval from specialists. Calls to other physicians is also made if necessary, and the fax and call process will be repeated. At the end of the call, a short satisfaction survey will optionally be administered.

Every suggestion will have a documented resolution: accepted, rejected and deferred. If the physician determines a medication and/or therapy change and optionally if there is agreement on the change in Step S78, the physician, for example, documents the therapy/medication change and transmits to appropriate destination or caller in Step S80. The physician is also asked to write the prescription, and send it to the patient or hand them over personally during an ulterior patient visit. The pharmacy is optionally informed of the new prescription and/or cancellation of an old prescription in Step S82.

Callers will inform prescribers that a confirmation letter will optionally be transmitted. In Step S84, patients are transmitted a confirmation letter, and in Step S86 the confirmation letter is sent to the physician.

Confirmation letters are manually generated either by support personnel from the notes taken by callers, or automatically generated by the medication review system using the data stored in the system regarding the resolution with the patient and physician. A manager optionally reviews and co-signs the letters. If the physician could not be contacted, a letter conveying this information is sent to the patient. Patients who have requested to receive a call-back for explanations are also contacted. In addition, if there is a need for an immediate change, the patient and/or physician is called back, as necessary. During the entire program, special care will be exercised in documenting adverse experiences.

If additional physicians need be contacted as determined in Step S90, the physician or specialist is called in Step S92, and an additional consultation is conducted with this additional physician, as described above. The process ends at Step S94.

Appendix A is a sample of the formatted information collected by the caller or pharmacist used when contacting the physician, or alternatively a sample of the information electronically transmitted to the physician. Appendix B is a sample of the information obtained from the patient experiencing multiple problems. Appendix C is a sample letter sent to the physician confirming participation of the patient in the program. Appendix D is a sample letter sent to the physician initial recommendations with the letter of Appendix C.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

APPENDIX A

1

Med Hx II Final
Med Hx III/Doctor Call Preparation Worksheet
Patient Name:
Patient I.D.#:

PATIENT DEMOGRAPHICS

PT NAME
8 Lancaster Drive
Scotia, NY 12302
518-399-5927 caucasian
Male
5 feet 10 inches shrunk from 6 feet
220 lbs. up and down (high as 230)
Retired nuclear engineer DOB: 9/7/33 (63 years)

BMI (31)

PHYSICIAN INFORMATION

Primary Physician
Dr. (Name)
1-518-399-2233 (internal medicine)
463 East Rd
Scotia, NY 12302

Other Physicians
Dr. (Name) cardiologist
2546 West Rd
Schenectady, NY 12309
Cardiologist Dr. (Name)
orthopedic

LIST OF CURRENT PRESCRIPTION MEDICATIONS:
(Purpose, response, satisfaction and adverse reactions as supplied by the patient)

| Medication | Strength | Route | Sig | Start Date | Use | Comments |
|---|---|---|---|---|---|---|
| Prilosec | 20mg | po | 1 QD | 1994 | reflux (had ge dilatation) | Dr. (Name) |
| Beconase | AQ (0.042%) | intranasal | 2 sprays in each nostril BID | 1995 | rhinitis | Dr. (Name) |
| Propranolol | 120mg | po | 1 QD | 1986 | acoustic neuroma removed in 1986 resulted in cluster headaches | Dr. (Name) |
| Colestid | 1 gm | po | 1 QID | 3/97 | | 2 in am 2 in afternoon, sometimes takes all at once Dr. (Name) |
| Zocor | 40mg | po | 1 QD | 9/96 | takes after dinner | Dr. (Name) |
| Diclofenac | 75mg | po | 1 BID | x 5 years | scopes on both knees ~ 1988, | Dr. (Name)/Dr. (Name)now |

| | | | | | torn miniscus, "arthritis in bothe knees" | prescribes just before bfast, closer to bedtime, works well. tries top get off, pain got worse. |
|---|---|---|---|---|---|---|
| Lac-Hydrin | 12% | topically | apply to feet prn | 1-2 years | dry feet--had a morton's neroma on foot | Dr. (Name) |
| Flu shot | | | | fall 1996 | | |

* Patient reports requiring cortisone/lidocaine shot for trigger finger once every year or two. No more one injection per flare-up *

Previous Medications:

Ticlid 250mg    8/24/96 (post coronary stent)
Nitrostat 0.4mg 8/20/96 (prior to angioplasty)
Imdur 60mg      8/20/96 (prior to angioplasty)
Metrogel 0.75%  3/22/96 last fill date
Acular 0.5%     3/22/96 last fill date
Azmacort        4/24/95 (spouse)

LIST OF CURRENT NON-PRESCRIPTION MEDICATIONS AND HOME REMEDIES:
(Purpose, response, satisfaction and adverse reactions as supplied by the patient)

| Medication | Strength | Route | Sig | Start Date | Use | Comments |
|---|---|---|---|---|---|---|
| apirin | 325 mg | po | qd | ~8/96 | "heart" | per Dr. (Name) |
| aspirin | 325 mg | po | 1-2 po prn headaches | | | uses once a month or two; at most two doses |

| | | | | | to relieve headache |
|---|---|---|---|---|---|
| Pseudoephedrine | 30 mg | po | 2 tablets qd for a few days | rhinitis | takes about once a month |
| Multiple Vitamin Alphabet | AARP formula # 358 Iron 18 mg | po | qd | | |
| Vitamin E | 400 iu | po | qd | | |
| Vitamin C | 500 mg | po | qd | | |
| Natural tears | | opth | pm | | uses maybe once a month |

Denies use of otc laxatives, acetaminophen, and nsaid's

PATIENT REPORTED MEDICATION ALLERGY AND ADVERSE DRUG REACTION DESCRIPTION:

Cholestid
GI Intolerance
At start of therapy (3/97), had heartburn and belching, resolved with slow titration of dosing .
The patient continues to ecive this therpay.

Propranolol
Patient reports suffering from short term memory loss since the initiation of propranolol. Reports difficulty remembering phone numbers and names. Short term memory loss has been reported as a rare occurrence with propranolol therapy. The onset of this symptom also coincides with the surgery for the removal of an acoustic neuroma. The patient continues to receive propranolol therapy.

PATIENT MEDICATION COMPLIANCE EVALUATION:

Patient appears compliant with chronic medications.

MEDICAL HISTORY/FAMILY HISTORY

| | | | | | |
|---|---|---|---|---|---|
| y | Allergic Rhinitis | n | Asthma | y | Arthritis (varius joints): knees, shoulders, trigger finger |
| n | COPD | n | Chronic Bronchitis | n | Emphysema | breathing difficulty last week in arizona: patient encouraged to inform MD at appt this afternoon

| | | | | | |
|---|---|---|---|---|---|
| n | Sinusitis | n | Generalized Anxiety D/O | n | Panic D/O |
| n | Depression | y | Bowel or stomach problems g-e dilatation | n | Diabetes |
| ? | High Blood Pressure | y | High Cholesterol | n | Epilepsy |

APPENDIX B

| | | | | | |
|---|---|---|---|---|---|
| y | Kidney Disease | y | Liver Disease | y | Migraines |
| y | Sleeping Difficulties (mother?) does nothing, wake up during night has to urinate | y | Stroke father ago 82 yo, heavy drinker | y | Heart Disease father died 3-4 years smoker, stroke children fine 2 girls, 40 and 36 |
| n | Osteoporosis | n | Cancer | n | ROS | y    Other conditions
"trigger finger"-bump on nerve or tendon
gets shot of cortisone---last one 2-3 months ago, gets once every two years. gets by Dr. (Name)

Hospitalizations angioplaststy
lost end of finger-8/96 ~same time as angioplasty----same day surgery

ER Visits
CP 8/96
Digit avulsion 8/96

Surgeries
acoustic neuroma removal (1988)
Morton's neruoma removal (2-3 years ago)

Blood Work, other tests
PSA measured last week
Thinks if lost weight, problems go away---wants to try redux: patient BMI 31; informed probably not a candidate; life style/eating change would be best avenue

Other questions

| | | |
|---|---|---|
| Vision Problems? | omitted | |
| Hearing Problems? | n | |
| Special Diet? | y-low fat | |
| Smoke? | n | |
| Caffeine? | y | 3 cups per day coffee |
| Alcohol? | y | not asked drinks per week |
| Recreational drugs | deferred | |
| Physical disability | y-knees difficulty climbing. and lifting heavy stuff/ walks/does yard work | |

Mental disability    n (has memory lapses)

Social History, Activities, Exercise retired x 4 years was a nuclear engineer
walks 1 1/2 miles 4 days per week Sexual History: Non Medication Birth Control not a problem, slowed down a bit
Patient assessment of health care and ability to impact outcome.
   What bothers you most about your current health problems?
1. arthirits in knees (annoying)  2. getting up a night (70% of time to urinate) 3. memory
   Do you feel you are getting better, staying the same, or getting worse?
knees, worse.. everything else the same
   What could be done to make you feel better?
losing weight
What questions do you have?
none

Problem:
*Allergic Rhinitis*

Medication Issue:

Precall Planning:

Involved Medications:
Beconase nasal spray

Relevant Past Medications:
Pseudoephedirine---didn't do a good job; uses periodically 2 tablets max/day for 2-3 days once/month

Cause of Issue/Problem:
Are the allergies seasonal or year round? not attributible to seasonal onset; worst in Jan/Feb sometimes worse than others What type of symptoms typically predominate?
   Congestion Can the patient identify particular triggers to their symptoms?
    Beniding over, relates it to acoustic neuroma removal "chopped through sinus?"; fluid evaluated for CSF; not CSF What additional treatments have been tried in the past?
tries pseudoephedrine
    Does the patient ever use antihistamines?
no
Has any particular treatment been more effective than any other?
beconase
Has the patient ever been treated prophylactically?
yes, on beconase What avoidance measures does the patient use if any to prevent symptoms? (non-pharmacologic measures)
none

Data to be collected/confirmed:

Therapeutic Goal:
Prevention of allergic symptoms.
Decrease in frequency, intensity and duration of symptoms.
Prevent a decrease in the patients normal activities of daily living secondary to allergies and thus improve the patients quality of life.

References:

Suggested Actions: None

Supporting Information:

Reason:

Supporting Information:

Summary of MD Response:

Problem:
*Angina*

Medication Issue:

Precall Planning:

Involved Medications:

Relevant Past Medications:
Imdur
Nitrostat
Ticlid

Cause of Issue/problem:
When did the patient first experience an episode of chest pain?
    What age? last year
    What were they doing?walking
experienced SOB last week in Arizona. Has an appt with cardiologist today, advised pt to relate this experience to physician

How often does the patient experience chest pain?
none since angioplasty
What type of activities precipitate the chest pain?
walking, but none since angioplasty What does the patient usually do when they experience chest pain?
rested, went away
Is the pain relieved with rest?yes Has the frequency or duration of the chest pain changed over the past few months?
no
In the past week, how many SL tablets has the patient had to use?
none no longer needs since angioplasty
Is there any family history of CAD?
no
Has the patient ever experienced an MI?
no
Does the patient have radiographic evidence of atherosclerosis?
yes; several follow-up EKG's have are reoprted as fine
    Data to be collected/confirmed:

Therapeutic Goal:
Decreased frequency of cardiac ischemia.
Decreased duration of cardiac ischemia.
Prevention of AMI.
Increased exercise tolerance.
Increased ability to perform activities of daily living.

References:

Suggested Actions: Not an active problem

Supporting information:

Reason:

Supporting information:

Summary of MD response:

ha angioplasty 8/96 and a stent. "blockage" noted during exercise test never needed sl nitro first noted when walking felt discomfort, rested, went away.

Problem:
*Hypercholesterolemia*

Medication Issue:
Elevated LDL cholesterol
Precall Planning:

Involved Medications:
Zocor 40mg        QD
Colestid 1gm       1 QID
patient takes Zocaor after meals; takes Colestid 2 caps BID; if forgets takes all four at once
    Relevant Past Medications:
Zocor 10mg and 20mg

Cause of Issue/problem:
When was the patient first told they had high cholesterol?
10 years ago What was the patients cholesterol when first diagnosed?
was ~ 260 total 9/96, HDL ~ 30, Ldl ??~230

What treatment has the patient received for their cholesterol?
    Diet?-yes
    Exercise?-yes
    Medication?-no initiated Zocor 9/96; Colestid 3/97

Does the patient have any evidence or history of CAD?

| CAD | Peripheral Vascular Disease | CNS |
|---|---|---|
| MI---no | Intermittent claudication--no | Stroke--no |
| Angina--yes | Renal artery stenosis---no | TIA's--??-memoery problems |
| CABG--no | Carotid bruits---no | |
| Angioplasty--Y | | |
| Angiographic evidence of disease--Y | | |

What risk factors does the patient have for the development of CAD?
    Male >45 years of age
    HTN-no, but on propranolol for cluster headaches, has reduced BP but has never been high
    Overweight Does the patient currently follow a low fat diet?
yes
Does the patient currently have a regular exercise program?
walks ~ 1 1/2 mile/day 4 days per week
Has the patient ever had other treatment for their cholesterol?
no
What was the patients most recent cholesterol levels? (3/97? before Colestid initiation); none since; appt with Dr. (Name) 4/21

| Total Cholesterol | 210 |
| --- | --- |
| LDL | ??? |
| HDL | 32 |
| Triglycerides | |

Data to be collected/confirmed:

| ALT | fine |
| --- | --- |
| AST | fine |
| Alk Phos | fine |
| Glucose | ok |
| Blood Pressure | very normal |

Therapeutic Goal:

| *Documented CAD* | *LDL< 100mg/dl* |
| --- | --- |
| 2 or more risk factors/no CAD | LDL< 130mg/dl |
| < 2 risk factors/no CAD | LDL< 160mg/dl |

Prevention of development/progression of CAD.

References:
NCEP guidelines.

Suggested Actions: Continue to monitor cholesterol with recent addition of Colestid; Increase Colestid as needed and tolerated based on LDL response.

Supporting information:

Reason: NCEP II guidelines. LDL goal 100mg/dL

Supporting information:

Summary of MD response:

Problem:
*Gastroesophageal Reflux Disease (GERD)*

Medication Issue:

Precall Planning:

Involved Medications:
Prilosec 20mg        QD
    Patient has been on prilosec for a long time. No other meds noted for treatment of reflux.
    Relevant Past Medications:

Cause of Issue/problem:
How long has the patient had problems with reflux?
    since starting on Voltaren per physician
Has the patient ever had any studies or tests done in evaluation of their reflux?
    had g-e "expansion" ~1994; previously had upper GI for diagnosis; documented acid into esophagus
What non-pharmacologic measures does the patient participate in? None needed; Prilosec relieves problem; eats whatever he likes with no difficulty
- Avoid postures, positions, and activities which tend to cause acid to reflux into the esophagus. *(bending over, exercise, lying supine after eating.)*--recognizes this a a trigger
- Avoid wearing constrictive clothing.
- Elevate the head of the bed six inches off the floor.--does not need to
- Eating smaller, less fatty, more frequent meals.
- Not eating within 3 hours of bedtime.
- Avoid precipitants such as coffee, citrus fruit juices, tomato products, chocolate, cigarettes, alcohol, spearmint, and peppermint.-no
- Weight loss.-
- Sugarless gum. (stimulates saliva secretion)

Does the patient use antacids to control reflux?
    no (very rarely): none in past month
    How often does the patient use antacids?
    very rarely
What other medical treatments have been tried in the past?
    none
Patient has had a trial off of Prilosec; needed medication reinitiated
    Data to be collected/confirmed:

Therapeutic Goal:

References:

Suggested Actions:Not an active problem

Supporting information:

Reason:

Supporting information:

Summary of MD response:

Problem:
*Cluster headache prophylaxis*

Medication Issue:
Patient reports short term memory loss attributed to initiation of propranolol.
Precall Planning:

Involved Medications:
Propranolo 120mg SR

Relevant Past Medications:

Cause of Issue/problem:

How long has had cluster headaches?
    since 1988 since removal of acoustic neuroma. reccomended by neurologist
    diagnosed as cluster headaches
What to take when they occur? none have occurred since start of Propranolol What type of migraines (cluster)?
    cluster headaches
Describe the ha's.
    has not had them since starting on
how often do they occur how long do they last? n/a best treatment? Propranolol works, but difficullty with memory precipitating factors?

Propranolol not a usual treatment for cluster headache prophylaxis; ? whether patient should have trial off prophylactic therapy as therapy has not been discontinued since 1988. ? referral to neurologist. Evaluation of short term memory loss. If dc propranolol need to use Senior's withdrawal suggestions and consider potential of change in BP.

Suggested Action: Consider evaluation of continued need for prophylactic therapy for cluster headaches Reason: Patient concern regarding memory loss; no trial off propranolol since initiation in 1988.

Problem:

Arthritis

Medication Issue:
Patient has been on Voltaren for long time (1988).
Precall Planning:

Involved Medications:
Diclofenac 75mg               BID

Relevant Past Medications:

Cause of Issue/Problem:
What is the cause of the patients pain? arthritis and s/p arthroscopy of knees; torn miniscus How long has he had?(1988)

Other treatments? iburpofen doesn't work; acetaminophen ineffective

Does this med work?yes; trial off 2-3 months ago; required reinitiation

Is it causing water retention and some of his other problems? no

Data to be collected/confirmed:

Therapeutic Goal:

References:

Suggested Actions: Not an active problem

Supporting Information:

Reason:

Supporting Information:

Summary of MD Response:

angiaplasty 8-9/96-----no MI just angina detected on exercise
memory problem---recalling names, seven digits, used to be able to remember stuff (was an engineer)

Third Issue:

APPENDIX C

July 29, 1997

IMPORTANT: PLACE IN THE FILE OF YOUR PATIENT

Dr. William T
116 Main Street
Pittsfield, N.C.

Richard C
255 ABC Rd.
Concord, N.C.

RE: Patient Medication History Review

Dear Dr. T:

We manage the pharmacy benefits for your patient's health care plan. We would like to schedule a convenient time for you to review with us your patient's medication regimen. One of our pharmacists will call your office to schedule a short telephone appointment.

As part of ongoing efforts to address quality of care and control costs, clinical pharmacists sometimes review aspects of pharmaceutical care with patients who are on complex regimens. Important therapeutic information gathered in this process can then be brought to the prescribers' attention.

Your patient, Mr.C, *has voluntarily enrolled in this program* and was interviewed on the telephone Terri Hix, RPh on 1/21/97. During the interview, Mr.C *authorized us to contact you for this review.*

What makes these reviews so informative for physicians is access to information that would not otherwise be readily available. For example, these reviews are based on all prescriptions filled at all Merck-Medco-affiliated pharmacies, written by all prescribing physicians involved in your patient's care, over an extended period of time. During our interview with your patient, we also gathered information about his current non-prescription medications, compliance habits, and adverse drug events. We discussed with the patient the purpose and goals of his regimen, and his expectations for those medications.

As a result of this conversation and using other information available to us, we have developed a list of medication issues and possible actions for your consideration. On the pages following this letter, you will find this list, together with your patient's medication profile. A clinical pharmacist will call you at the appointed time to confirm the accuracy of the data collected and to obtain your evaluation of, and response to, our suggestions. After our telephone conversation with you, we will send letters to both you and your patient summarizing your decisions.

Merck-Medco Managed Care, L.L.C., PAID Prescriptions, L.L.C. and Merck-Medco Rx Services are subsidiaries of Merck & Co., Inc.

Due to the current scope of this program, it may be necessary for us to contact you separately on behalf of other patients of yours who enroll in this program. We apologize for this inconvenience. If you would like to contact us regarding this program, please call us at 1-800-440-0473 and ask for a Personal Medication Review pharmacist.

We appreciate your support in our efforts to provide your patients with high quality and cost effective health care services.

Respectfully,

Program Manager, PMR

Merck-Medco Managed Care, L.L.C., PAID Prescriptions, L.L.C. and Merck-Medco Rx Services are subsidiaries of Merck & Co., Inc.

APPENDIX D

MEDICATION HISTORY FOR

The following suggestions are based upon the information that was obtained directly from the patient by their pharmacist during a telephone Personal Medication Review, and upon the information that is currently in our patient medication profiles. This information may be incomplete. The suggested actions may need to be modified to account for other individual patient factors, and/or relevant information that you may be aware of regarding this patient.

MEDICATION ISSUES AND SUGGESTED ACTIONS/REASONS:

| MEDICATION ISSUES | MEDICATION | CONSIDERATIONS | REASONS |
| --- | --- | --- | --- |
| Patient reports unstable angina and long term Inderal use | Minitran patches Inderal Nitrostat Vasotec Coumadin Aspirin Lasix | Is the Inderal contributing to this patient's depression? | Inderal may exacerbate depression |
| Patient reports long term trazodone use | Trazodone | Is this patient a candidate for a trial of tapering off of trazodone? | Per AHCPR guidelines |
| Patient reports new pain in joints and "muscle behind my knee" | Vasotec (now d/c'd) Pravachol Cozaar | Although the incidence is low, consider measuring a CPK (If not already done) to check for Pravachol-induced myalgia. | Incidence of muscle cramps or arthralgias is similar between Vasotec and Cozaar. |

LIST OF CURRENT PRESCRIPTION MEDICATIONS:
(Purpose, response, satisfaction and adverse reactions as supplied by the patient)

| Medication | Strength | Route | Sig | Start Date | Use | Comments |
| --- | --- | --- | --- | --- | --- | --- |
| Clonidine | 200mcg | PO | 1 tab BID | 1/3/97 | HTN | pt uses 1 tab/day while still on the patch |
| Catapres Patch | 0.2mg | TOP | 1 patch QFRI am | several yrs | HTN | will dc when supply runs out |
| Vasotec | 5mg | PO | 1 tab QAM | 1/15/97 | CHF,HTN | pt reports edema resolving |
| Lasix | 40mg | PO | 1 tab QAM | several yrs | HTN, CHF | |
| Propranolol | 10mg | PO | 1 tab BID | many yrs | Angina | Pt now uses TID |
| Minitran Patch | 0.4mg | TOP | Apply QAM and remove QHS | several yrs | Angina | Pt prefers this brand |
| Nitrostat | 400mcg | SL | 1 tab SL prn chest pain, MR x2 | several yrs | Angina | uses on a daily basis |
| Pravachol | 20mg | PO | 1 QHS | 7/96 | Hypercholesterolemia | |
| Coumadin | 5mg | PO | 1QD | several yrs | Anticoagulant | now takes 5mg-5mg-2.5mg and repeats QD |
| Trazodone | 100mg | PO | 2 1/2 tabs QHS | many yrs | Depression | |
| Lorazepam | 1mg | PO | 1 QD | many yrs | Sleep,anxiety | |

Merck-Medco Managed Care, L.L.C., PAID Prescriptions, L.L.C. and Merck-Medco Rx Services are subsidiaries of Merck & Co., Inc.

| LIST OF CURRENT PRESCRIPTION MEDICATIONS: |||||||
|---|---|---|---|---|---|---|
| (Purpose, response, satisfaction and adverse reactions as supplied by the patient) |||||||
| Medication | Strength | Route | Sig | Start Date | Use | Comments |
| Donnatal |  | PO | 1 tab prn esophagitis | 10/96 | Inflamed esophagus | has not used any in several weeks |

On 1/29/97, Mr. Current reported his Vasotec will be discontinued and Cozaar will be started at 50mg QAM. He also reports he is now using Minitran Patches 0.6mg/hr QD.

| LIST OF CURRENT NON-PRESCRIPTION MEDICATIONS AND HOME REMEDIES: |||||||
|---|---|---|---|---|---|---|
| (Purpose, response, satisfaction and adverse reactions as supplied by the patient) |||||||
| Medication | Strength | Route | Sig | Start Date | Use | Comments |
| Acetaminophen | 500mg | PO | 2 tabs prn | many yrs | HA 2° to nitrates | HA's are relieved |
| Metamucil |  | PO | 3 tsp in water BID | many yrs | constipation | uses daily |
| Per Diem |  | PO | 2-3 tsp water | many yrs | severe constipation | uses approx. 1x/week |
| Vitamin C | 500mg | PO | 1 QD | 6-8 months ago | per Dr. Thompson |  |
| Vitamin E | 400 IU | PO | 1 QD | several yrs | per Dr. Thompson |  |
| Aspirin | 81mg | PO | 1 QD | several yrs | per Dr. Thompson |  |

PATIENT REPORTED MEDICATION ALLERGY AND ADVERSE DRUG REACTION DESCRIPTION:

Patient denies any drug allergies

Patient reports the following adverse reactions: 1) Relafen-severe stomach upset-reaction occurred last fall after a few days of therapy for arthritis-pt 's symptoms have resolved with the drug being discontinued. Patient has not been rechallenged. 2) Ismo-patient started med in Dec. 1996 and after 3-4 days felt terrible(described being dizzy and feeling as if he would have a heart attack). Med was discontinued and symptoms subsided-has not been rechallenged. 3) Norvasc-patient experienced edema especially when dose was doubled to 10mg. However this has resolved and pt has not been rechallenged. This occurred in late December 1996/early January 1997.

Patient also reports a nitrate headache that is relieved by acetaminophen use.

Patient phoned in on 1-29-97 to state his Vasotec was being discontinued due to muscle and joint pains in his legs. He descibes the pain as a new joint pain as well as a "knot" behind his knee. The pain has improved somewhat since discontinuation of Vasotec, but the "knot" behind his knee has not gone away. He reports that the color of his urine is not red or brown.

Merck-Medco Managed Care, L.L.C., PAID Prescriptions, L.L.C. and Merck-Medco Rx Services are subsidiaries of Merck & Co., Inc.

PATIENT MEDICATION COMPLIANCE EVALUATION:
Patient has a good understanding ot the purpose of his medications. He denies having any difficulty remembering to take his medications since he has started using a pill box. He is somewhat concerned over the cost of his medications as his insurance has recently changed to the pensioner's plan where each med(brand or generic) is a $20.00 copay per 90 day supply unless the cost of the generic is less than the $20.00..

Merck-Medco Managed Care, L.L.C., PAID Prescriptions, L.L.C. and Merck-Medco Rx Services are subsidiaries of Merck & Co., Inc.

What is claimed is:

1. An interactive computer assisted method of reviewing, analyzing, and prescribing a patient one or more medications using a computer and a user associated therewith, the user coordinating said interactive computer assisted method with at least one physician and at least one pharmacist, prior to the prescribing the patient of the one or more medications, said method comprising the steps of:

(a) pre-selecting patients to obtain a preliminary set of patients eligible for said interactive computer assisted method responsive to first predetermined criteria;

(b) filtering the preliminary set of patients to identify and form a secondary set of patients from the preliminary set of patients having a greater likelihood of benefiting from said interactive computer assisted method responsive to second predetermined criteria;

(c) enrolling at least one patient from the secondary set of patients;

(d) communicating, by the user, with the at least one patient to obtain information to assist the user in determining whether at least one of therapy and medication changes are appropriate;

(e) preliminarily evaluating, by the user, whether the at least one of therapy and medication changes are appropriate responsive to the information;

(f) communicating, by the user, to a physician, the at least one of therapy and medication changes and the information;

(g) determining, by the physician, whether the at least one of therapy and medication changes are appropriate responsive to the information, and prescribing at least one of the at least one of therapy and medication changes, at least one of other therapy and medication changes, and no therapy and medication changes for the at least one patient;

(h) confirming, by the user, the prescribing by the physician with the pharmacist for the at least one of the at least one of therapy and medication changes, at least one of other therapy and medication changes, and no therapy and medication changes for the at least one patient, and receiving comments from the pharmacist relating thereto; and (i) communicating, by the user, to the physician, the comments received from the pharmacist at least when the comments include a pharmacist opinion with respect to the at least one of therapy and medication changes and the information determined by the physician.

2. An interactive computer assisted method according to claim 1, further comprising the step of confirming, by the user, the prescribing by the physician with the patient.

3. An interactive computer assisted method according to claim 1, further comprising the step of confirming, by the user, the prescribing by the physician with a pharmacist for possible medication changes.

4. An interactive computer assisted method according to claim 1, further comprising the step of communicating, by the user, to a pharmacist, to obtain additional information to further assist the user in determining whether the at least one of therapy and medication changes are appropriate.

5. An interactive computer assisted method according to claim 1, wherein the information includes at least one of patient demographics, patient's physician(s), current medications, medication use pattern, over the counter medication use, patient understanding of treatment goals, adverse effects, compliance history, medical history, family history, hospitalization history, pertinent laboratory work, patient concerns and assessment, and patient satisfaction assessment.

6. An interactive computer assisted method according to claim 1, further comprising the steps of confirming, by the user, the prescribing by the physician with a pharmacist of a mail order pharmacy for possible medication changes, and mailing medication to the patient.

7. An interactive computer assisted method of reviewing, analyzing, and prescribing a patient one or more medications using a computer and a user associated therewith, the user coordinating said interactive computer assisted method with at least one physician and at least one pharmacist, prior to the prescribing the patient of the one or more medications, said method comprising the steps of:

(a) pre-selecting patients to obtain a preliminary set of patients eligible for said interactive computer assisted method responsive to first predetermined criteria;

(b) filtering the preliminary set of patients to identify and form a secondary set of patients from the preliminary set of patients having a greater likelihood of benefiting from said interactive computer assisted method responsive to second predetermined criteria;

(c) enrolling, by at least one of the user using the computer and the computer, at least one patient from the secondary set of patients;

(d) communicating with the at least one patient to obtain information to assist the user in determining whether at least one of therapy and medication changes are appropriate, the information including at least one of patient demographics, patient's physician(s), current medications, medication use pattern, over the counter medication use, patient understanding of treatment goals, adverse effects, compliance history, medical history, family history, hospitalization history, pertinent laboratory work, patient concerns and assessment, and patient satisfaction assessment;

(e) communicating, by the user, to the pharmacist, to obtain additional information to further assist the user in determining whether the at least one of therapy and medication changes are appropriate;

(f) preliminarily evaluating, by the user, whether the at least one of therapy and medication changes are appropriate responsive to the information and the additional information;

(g) communicating, by the user, to a physician, the at least one of therapy and medication changes, the information, and the additional information;

(h) determining, by the physician, whether the at least one of therapy and medication changes are appropriate responsive to the information, and prescribing at least one of the at least one of therapy and medication changes, at least one of other therapy and medication changes, and no therapy and medication changes for the at least one patient;

(i) confirming, by the user, the prescribing by the physician with the patient;

(j) confirming, by the user, the prescribing by the physician with the pharmacist for the at least one of the at least one of therapy and medication changes, at least one of other therapy and medication changes, and no therapy and medication changes for the at least one patient, and receiving comments from the pharmacist relating thereto; and (k) communicating, by the user, to the physician, the comments received from the pharmacist at least when the comments include a pharmacist opinion with respect to the at least one of therapy and medication changes and the information determined by the physician; and (l) mailing medication to the patient responsive to at least one of the medication changes and the other medication changes.

8. An interactive computer assisted method of reviewing, analyzing, and prescribing a patient one or more medications using a computer and a user associated therewith, the user coordinating said interactive computer assisted method with at least one physician and at least one pharmacist, prior to the prescribing the patient of the one or more medications, said method comprising the steps of:

(a) pre-selecting patients to obtain a preliminary set of patients eligible for said interactive computer assisted method responsive to first predetermined criteria;

(b) filtering the preliminary set of patients to identify and form a secondary set of patients from the preliminary set of patients having a greater likelihood of benefiting from said interactive computer assisted method responsive to second predetermined criteria;

(c) enrolling, by the computer, at least one patient from the secondary set of patients;

(d) communicating with the at least one patient to obtain information to assist the user in determining whether at least one of therapy and medication changes are appropriate;

(e) preliminarily evaluating whether the at least one of therapy and medication changes are appropriate responsive to the information;

(f) communicating by the computer, to a physician, the at least one of therapy and medication changes and the information; and (g) determining, by the physician, whether the at least one of therapy and medication changes are appropriate responsive to the information, and prescribing at least one of the at least one of therapy and medication changes, at least one of other therapy and medication changes, and no therapy and medication changes for the at least one patient; and (h) confirming, by the user, the prescribing by the physician with the pharmacist for the at least one of the at least one of therapy and medication changes, at least one of other therapy and medication changes, and no therapy and medication changes for the at least one patient, and receiving comments from the pharmacist relating thereto; and (i) communicating, by the user, to the physician, the comments received from the pharmacist at least when the comments include a pharmacist opinion with respect to the at least one of therapy and medication changes and the information determined by the physician.

9. An interactive computer assisted method of reviewing, analyzing, and prescribing a patient one or more medications using a computer and a user associated therewith, the user coordinating said interactive computer assisted method with at least one physician and at least one pharmacist, prior to the prescribing the patient of the one or more medications, said method comprising the steps of:

(a) pre-selecting patients to obtain a preliminary set of patients eligible for said interactive computer assisted method responsive to first predetermined criteria;

(b) filtering the preliminary set of patients to identify and form a secondary set of patients from the preliminary set of patients having a greater likelihood of benefiting from said interactive computer assisted method responsive to second predetermined criteria;

(c) enrolling, by the at least one of the user and the computer, at least one patient from the secondary set of patients;

(d) communicating, by the at least one of the user and the computer, with the at least one patient to obtain information to assist the user in determining whether at least one of therapy and medication changes are appropriate;

(e) preliminarily evaluating, by the at least one of the user and the computer, whether the at least one of therapy and medication changes are appropriate responsive to the information;

(f) communicating, by the at least one of the user and the computer, to a physician, the at least one of therapy and medication changes and the information; and (g) determining, by the physician, whether the at least one of therapy and medication changes are appropriate responsive to the information, and prescribing at least one of the at least one of therapy and medication changes, at least one of other therapy and medication changes, and no therapy and medication changes for the at least one patient;

(h) confirming, by the user, the prescribing by the physician with the pharmacist for the at least one of the at least one of therapy and medication changes, at least one of other therapy and medication changes, and no therapy and medication changes for the at least one patient, and receiving comments from the pharmacist relating thereto; and (i) communicating, by the user, to the physician, the comments received from the pharmacist at least when the comments include a pharmacist opinion with respect to the at least one of therapy and medication changes and the information determined by the physician.

10. An interactive computer assisted method according to claim 9, further comprising the step of confirming, by the user, the prescribing by the physician with the patient.

11. An interactive computer assisted method according to claim 9, further comprising the step of confirming, by the user, the prescribing by the physician with a pharmacist for possible medication changes.

12. An interactive computer assisted method according to claim 9, further comprising the step of communicating, by the user, to a pharmacist, to obtain additional information to further assist the user in determining whether the at least one of therapy and medication changes are appropriate.

13. An interactive computer assisted method according to claim 9, wherein the information includes at least one of patient demographics, patient's physician(s), current medications, medication use pattern, over the counter medication use, patient understanding of treatment goals, adverse effects, compliance history, medical history, family history, hospitalization history, pertinent laboratory work, patient concerns and assessment, and patient satisfaction assessment.

14. An interactive computer assisted method according to claim 9, further comprising the steps of confirming, by the user, the prescribing by the physician with a pharmacist of a mail order pharmacy for possible medication changes, and mailing medication to the patient.

15. A computer program memory, storing computer instructions to implement an interactive computer assisted method of reviewing, analyzing, and prescribing a patient one or more medications using a computer and a user associated therewith, the user coordinating said interactive computer assisted method with at least one physician and at least one pharmacist, prior to the prescribing the patient of the one or more medications, the computer instructions including:

(a) pre-selecting patients to obtain a preliminary set of patients eligible for said interactive computer assisted method responsive to first predetermined criteria;

(b) filtering, by at least one of the user and the computer, the preliminary set of patients to identify and form a secondary set of patients from the preliminary set of patients having a greater likelihood of benefiting from said interactive computer assisted method responsive to second predetermined criteria;

(c) enrolling, by the at least one of the user and the computer, at least one patient from the secondary set of patients;

(d) communicating, by the at least one of the user and the computer, with the at least one patient to obtain information to assist the user in determining whether at least one of therapy and medication changes are appropriate;

(e) preliminarily evaluating, by the at least one of the user and the computer, whether the at least one of therapy and medication changes are appropriate responsive to the information;

(f) communicating, by the at least one of the user and the computer, to a physician, the at least one of therapy and medication changes and the information; and (g) determining, by the physician, whether the at least one of therapy and medication changes are appropriate responsive to the information, and prescribing at least one of the at least one of therapy and medication changes, at least one of other therapy and medication changes, and no therapy and medication changes for the at least one patient;

(h) confirming, by the user, the prescribing by the physician with the pharmacist for the at least one of the at least one of therapy and medication changes, at least one of other therapy and medication changes, and no therapy and medication changes for the at least one patient, and receiving comments from the pharmacist relating thereto; and (i) communicating, by the user, to the physician, the comments received from the pharmacist at least when the comments include a pharmacist opinion with respect to the at least one of therapy and medication changes and the information determined by the physician.

16. A computer program memory according to claim 15, further comprising the instruction of confirming, by the user, the prescribing by the physician with the patient.

17. A computer program memory according to claim 15, further comprising the instruction of confirming, by the user, the prescribing by the physician with a pharmacist for possible medication changes.

18. A computer program memory according to claim 15, further comprising the instructions of communicating, by the user, to a pharmacist, to obtain additional information to further assist the user in determining whether the at least one of therapy and medication changes are appropriate.

19. A computer program memory according to claim 15, wherein the information includes at least one of patient demographics, patient's physician(s), current medications, medication use pattern, over the counter medication use, patient understanding of treatment goals, adverse effects, compliance history, medical history, family history, hospitalization history, pertinent laboratory work, patient concerns and assessment, and patient satisfaction assessment.

20. A computer program memory according to claim 15, further comprising the instructions of confirming, by the user, the prescribing by the physician with a pharmacist of a mail order pharmacy for possible medication changes, and mailing medication to the patient.

* * * * *